(12) United States Patent
Thompson et al.

(10) Patent No.: US 11,944,007 B2
(45) Date of Patent: *Mar. 26, 2024

(54) ORGANIC PHOTOSENSITIVE DEVICES COMPRISING ARYL SQUARAINES AND METHODS OF MAKING THE SAME

(71) Applicants: THE REGENTS OF THE UNIVERSITY OF MICHIGAN, Ann Arbor, MI (US); UNIVERSITY OF SOUTHERN CALIFORNIA, Los Angeles, CA (US)

(72) Inventors: Mark E. Thompson, Anaheim, CA (US); Stephen R. Forrest, Ann Arbor, MI (US); Guodan Wei, San Ramon, CA (US); Siyi Wang, Hillsboro, OR (US); Lincoln Hall, St. Joseph (TT); Viacheslav V. Diev, Wilmington, DE (US); Xin Xiao, Ann Arbor, MI (US)

(73) Assignees: The Regents of the University of Michigan, Ann Arbor, MI (US); University of Southern California, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/449,881

(22) Filed: Jun. 24, 2019

(65) Prior Publication Data
US 2020/0303660 A1    Sep. 24, 2020

Related U.S. Application Data

(60) Division of application No. 14/853,256, filed on Sep. 14, 2015, now Pat. No. 10,333,079, which is a continuation of application No. 13/368,040, filed on Feb. 7, 2012, now abandoned.

(60) Provisional application No. 61/479,231, filed on Apr. 26, 2011, provisional application No. 61/441,153, filed on Feb. 9, 2011.

(51) Int. Cl.
| | |
|---|---|
| *C09B 57/00* | (2006.01) |
| *B82Y 10/00* | (2011.01) |
| *C09K 11/06* | (2006.01) |
| *H01G 9/20* | (2006.01) |
| *H10K 85/60* | (2023.01) |
| *H10K 30/20* | (2023.01) |
| *H10K 85/20* | (2023.01) |

(52) U.S. Cl.
CPC .......... *H10K 85/6572* (2023.02); *B82Y 10/00* (2013.01); *C09B 57/007* (2013.01); *C09B 57/008* (2013.01); *C09K 11/06* (2013.01); *H01G 9/2059* (2013.01); *H10K 85/631* (2023.02); *H10K 85/633* (2023.02); *H10K 85/657* (2023.02); *C07C 2601/04* (2017.05); *C09K 2211/1007* (2013.01); *C09K 2211/1011* (2013.01); *C09K 2211/1014* (2013.01); *C09K 2211/1029* (2013.01); *H10K 30/211* (2023.02); *H10K 85/211* (2023.02); *H10K 85/626* (2023.02); *Y02E 10/549* (2013.01)

(58) Field of Classification Search
CPC ... C09B 57/007; H10K 85/654; H10K 85/656
See application file for complete search history.

(56) References Cited

U.S. PATENT DOCUMENTS

| | | | |
|---|---|---|---|
| 3,824,099 A | 7/1974 | Champ et al. | |
| 6,836,383 B1 | 12/2004 | Ozawa et al. | |
| 10,297,775 B2 * | 5/2019 | Lassiter | H10K 30/821 |
| 10,333,079 B2 * | 6/2019 | Thompson | H01G 9/2059 |
| 11,352,500 B2 * | 6/2022 | Rosselli | H10K 30/82 |
| 2003/0082329 A1 * | 5/2003 | Shimizu | G11B 7/249 |
| | | | 428/64.4 |
| 2007/0105988 A1 | 5/2007 | Shimizu et al. | |
| 2010/0065112 A1 | 3/2010 | Thompson et al. | |

(Continued)

FOREIGN PATENT DOCUMENTS

| | | |
|---|---|---|
| EP | 0172321 | 2/1986 |
| EP | 1970959 | 9/2008 |

(Continued)

OTHER PUBLICATIONS

Z. Lu et al., 91 Synthetic Metals, 233-235 (1997) (Year: 1997).*
Bagnis, Diego, et al: Marked Alkyl- vs Alkenyl-Substitutent Effects on Squaraine Dye Solid-State Structure, Carrier Mobility, and Bulk-Heterojunction Solar Cell Efficiency, Journal of the American Chemical Society, vol. 132, No. 12, (Mar. 2010), pp. 4074-4075.
Forster, M., et al.: Squarilium Dyes. Their Infrared and Resonance Raman Spectra and possible use in Redox Reactions for Solar-Energy Conversion. J. Chem. Soc. Faraday Trans. 1, vol. 78. (1982). pp. 1847-1866.

(Continued)

*Primary Examiner* — Alexander R Pagano
(74) *Attorney, Agent, or Firm* — Finnegan, Henderson, Farabow, Garrett & Dunner, LLP

(57) ABSTRACT

There is disclosed squaraine compounds of formula I:

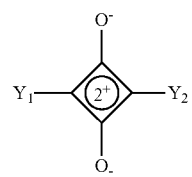

wherein each of $Y_1$ and $Y_2$ is independently chosen from an optionally substituted amino group and an optionally substituted aryl group. Also described are organic optoelectronic devices comprising a Donor-Acceptor heterojunction that is formed from one or more of the squaraine compounds. A method of making the disclosed device, which may include one or more sublimation step for depositing said squaraine compound, is also disclosed.

9 Claims, 7 Drawing Sheets

(56) References Cited

U.S. PATENT DOCUMENTS

2015/0207088 A1* 7/2015 Forrest .................. H10K 71/12
   438/74
2020/0303660 A1* 9/2020 Thompson ......... H10K 85/6572
2021/0288261 A1* 9/2021 Forrest .................. H10K 30/30

FOREIGN PATENT DOCUMENTS

| JP | 60-169453 | 9/1985 |
| JP | 63-132246 | 6/1988 |
| JP | 1-146845 | 6/1989 |
| JP | 1-146846 | 6/1989 |
| JP | 2003-109676 | 4/2003 |
| WO | WO-2006-041156 | 4/2006 |
| WO | WO-2007-049579 | 5/2007 |

OTHER PUBLICATIONS

Fu, Na, et al: Squaraine Rotaxanes with Boat Conformation Macrocycles, The Journal of Organic Chemistry, vol. 74, No. 17, (Sep. 2009), pp. 6462-6468.

International Search Report for PCT/US2012/024131 dated Aug. 28, 2012.

Merritt, V.Y., et al: Organic solar cells of hydroxy squarylium. Applied Physics Letters. vol. 29, No. 7, (Jan. 1976). pp. 414-415.

Neuse, Eberhard W., et al: Dianilino derivatives of squaric acid, The Journal of Organic Chemistry, vol. 39, No. 26, (Dec. 1974), pp. 3881-3887.

Oguz, Umut, et al: One-Pot Synthesis of Squaraine Fluoroionophores, The Journal of Organic Chemistry, vol. 63, No. 17, (Aug. 1998), pp. 6059-6060.

Ros-Lis, Jose V., et al: Colorimetric Signaling of Large Aromatic Hydrocarbons via the Enhancement of Aggregation Processes, Organic Letters, vol. 7, No. 12, (Jun. 2005), pp. 2337-2339.

Silvestri, Fabio, et al: Efficient Squaraine-Based Solution Processable Bulk-Heterojunction Solar Cells, Journal of the American Chemical Society, vol. 130, No. 52, (Dec. 2008), pp. 17640-17641.

Sprenger, Dr H-E, and Dr Wziegenbein: "Dr. H.-E. Sprenger and Dr. W. Ziegenbein". Angewandte Chemie. Wiley-V C Hverlag GmbH & Co. KGAA. DE. vol. 78. No. 20. (Oct. 1966). pp. 937-938.

Wei, Guodan, et al: Efficient, Ordered Bulk Heterojunction Nanocrystalline Solar Cells by Annealing of Ultrathin Squaraine Thin Films, Nano Letters, vol. 10, No. 9, (Sep. 2010), pp. 3555-3559.

Wei, Guodan, et al: Solution-Processed Squaraine Bulk Heterojunction Photovoltaic Cells, ACS NANO, vol. 4, No. 4, (Apr. 2010), pp. 1927-1934.

Written Opinion for PCT/US2012/024131 dated Aug. 28, 2012.

* cited by examiner

ORGANIC PHOTOSENSITIVE DEVICES COMPRISING ARYL SQUARAINES AND METHODS OF MAKING THE SAME

CROSS-REFERENCE TO RELATED APPLICATIONS

This application claims priority to U.S. Provisional Application No. 61/441,153, filed on Feb. 9, 2011, and 61/479,231, filed on Apr. 26, 2011, both of which are incorporated herein by reference in their entirety.

STATEMENT REGARDING FEDERALLY SPONSORED RESEARCH

The subject matter of this application was prepared with U.S. Government support under Contract No. DE-FG36-08GO18022 awarded by U.S. Department of Energy, Center for Energy Nanoscience, and Contract Nos. DE-SC0001013 and DE-SC0000957. The government has certain rights in the subject matter of this application.

JOINT RESEARCH AGREEMENT

The subject matter of this application was made by, on behalf of, and/or in connection with one or more of the following parties to a joint university-corporation research agreement: University of Michigan, University of Southern California, and Global Photonic Energy Corporation. The agreement was in effect on and before the date the claimed invention was made, and the claimed invention was made as a result of activities undertaken within the scope of the agreement.

The present disclosure generally relates to novel squaraine compounds, which may be useful in preparing organic photosensitive optoelectronic devices having a heterojunction comprising one or more of said squaraines. Methods of making such devices are also disclosed, which may include depositing the squaraine compound by spin-casting followed by thermal annealing.

Optoelectronic devices rely on the optical and electronic properties of materials to either produce or detect electromagnetic radiation electronically or to generate electricity from ambient electromagnetic radiation.

Photosensitive optoelectronic devices convert electromagnetic radiation into electricity. Solar cells, also called photovoltaic (PV) devices, are a type of photosensitive optoelectronic device that is specifically used to generate electrical power. PV devices, which may generate electrical energy from light sources other than sunlight, can be used to drive power consuming loads to provide, for example, lighting, heating, or to power electronic circuitry or devices such as calculators, radios, computers or remote monitoring or communications equipment. These power generation applications also often involve the charging of batteries or other energy storage devices so that operation may continue when direct illumination from the sun or other light sources is not available, or to balance the power output of the PV device with a specific application's requirements. As used herein the term "resistive load" refers to any power consuming or storing circuit, device, equipment or system.

Another type of photosensitive optoelectronic device is a photoconductor cell. In this function, signal detection circuitry monitors the resistance of the device to detect changes due to the absorption of light.

Another type of photosensitive optoelectronic device is a photodetector. In operation a photodetector is used in conjunction with a current detecting circuit which measures the current generated when the photodetector is exposed to electromagnetic radiation and may have an applied bias voltage.

A detecting circuit as described herein is capable of providing a bias voltage to a photodetector and measuring the electronic response of the photodetector to electromagnetic radiation.

These three classes of photosensitive optoelectronic devices may be characterized according to whether a rectifying junction as defined below is present and also according to whether the device is operated with an external applied voltage, also known as a bias or bias voltage. A photoconductor cell does not have a rectifying junction and is normally operated with a bias. A PV device has at least one rectifying junction and is operated with no bias. A photodetector has at least one rectifying junction and is usually but not always operated with a bias. Typically, a photovoltaic cell provides power to a circuit, device or equipment. A photodetector or photoconductor provides a signal or current to control detection circuitry, or the output of information from the detection circuitry but does not provide power to the circuitry, device or equipment.

Traditionally, photosensitive optoelectronic devices have been constructed of a number of inorganic semiconductors, e.g., crystalline, polycrystalline and amorphous silicon, gallium arsenide, cadmium telluride and others. Herein the term "semiconductor" denotes materials which can conduct electricity when charge carriers are induced by thermal or electromagnetic excitation. The term "photoconductive" generally relates to the process in which electromagnetic radiant energy is absorbed and thereby converted to excitation energy of electric charge carriers so that the carriers can conduct, i.e., transport, electric charge in a material. The terms "photoconductor" and "photoconductive material" are used herein to refer to semiconductor materials which are chosen for their property of absorbing electromagnetic radiation to generate electric charge carriers.

PV devices may be characterized by the efficiency with which they can convert incident solar power to useful electric power. Devices utilizing crystalline or amorphous silicon dominate commercial applications, and some have achieved efficiencies of 23% or greater. However, efficient crystalline-based devices, especially of large surface area, are difficult and expensive to produce due to the problems inherent in producing large crystals without significant efficiency-degrading defects. On the other hand, high efficiency amorphous silicon devices still suffer from problems with stability. Present commercially available amorphous silicon cells have stabilized efficiencies between 4 and 8%. More recent efforts have focused on the use of organic photovoltaic cells to achieve acceptable photovoltaic conversion efficiencies with economical production costs.

PV devices may be optimized for maximum electrical power generation under standard illumination conditions (i.e., Standard Test Conditions which are 1000 W/m$^2$, AM1.5 spectral illumination), for the maximum product of photocurrent times photovoltage. The power conversion efficiency of such a cell under standard illumination conditions depends on the following three parameters: (1) the current under zero bias, i.e., the short-circuit current $I_{SC}$, in Amperes (2) the photovoltage under open circuit conditions, i.e., the open circuit voltage $V_{OC}$, in Volts and (3) the fill factor, ff.

PV devices produce a photo-generated current when they are connected across a load and are irradiated by light. When irradiated under infinite load, a PV device generates its maximum possible voltage, V open-circuit, or $V_{OC}$. When irradiated with its electrical contacts shorted, a PV device generates its maximum possible current, I short-circuit, or $I^{SC}$. When actually used to generate power, a PV device is connected to a finite resistive load and the power output is given by the product of the current and voltage. I×V. The maximum total power generated by a PV device is inherently incapable of exceeding the product, $I_{SC} \times V_{OC}$. When the load value is optimized for maximum power extraction, the current and voltage have the values, $I_{max}$ and $V_{max}$, respectively.

A figure of merit for PV devices is the fill factor, ff, defined as:

$$ff = \{I_{max}V_{max}\}/\{I_{SC}V_{OC}\} \quad (1)$$

where ff is always less than 1, as $I_{SC}$ and $V_{OC}$ are never obtained simultaneously in actual use. Nonetheless, as ff approaches 1, the device has less series or internal resistance and thus delivers a greater percentage of the product of $I_{SC}$ and $V_{OC}$ to the load under optimal conditions. Where $P_{inc}$ is the power incident on a device, the power efficiency of the device, $\eta_P$, may be calculated by:

$$\eta_P = ff * (I_{SC}*V_{OC})/P_{inc}$$

When electromagnetic radiation of an appropriate energy is incident upon a semiconductive organic material, for example, an organic molecular crystal (OMC) material, or a polymer, a photon can be absorbed to produce an excited molecular state. This is represented symbolically as $S_0 + h\nu \Psi S_0^*$. Here $S_0$ and $S_0^*$ denote ground and excited molecular states, respectively. This energy absorption is associated with the promotion of an electron from a bound state in the HOMO energy level, which may be a B-bond, to the LUMO energy level, which may be a B*-bond, or equivalently, the promotion of a hole from the LUMO energy level to the HOMO energy level. In organic thin-film photoconductors, the generated molecular state is generally believed to be an exciton, i.e., an electron-hole pair in a bound state which is transported as a quasi-particle. The excitons can have an appreciable life-time before geminate recombination, which refers to the process of the original electron and hole recombining with each other, as opposed to recombination with holes or electrons from other pairs. To produce a photocurrent the electron-hole pair becomes separated, typically at a donor-acceptor interface between two dissimilar contacting organic thin films. If the charges do not separate, they can recombine in a germinant recombination process, also known as quenching, either radiatively, by the emission of light of a lower energy than the incident light, or non-radiatively, by the production of heat. Either of these outcomes is undesirable in a photosensitive optoelectronic device.

Electric fields or inhomogeneities at a contact may cause an exciton to quench rather than dissociate at the donor-acceptor interface, resulting in no net contribution to the current. Therefore, it is desirable to keep photogenerated excitons away from the contacts. This has the effect of limiting the diffusion of excitons to the region near the junction so that the associated electric field has an increased opportunity to separate charge carriers liberated by the dissociation of the excitons near the junction.

To produce internally generated electric fields which occupy a substantial volume, the usual method is to juxtapose two layers of material with appropriately selected conductive properties, especially with respect to their distribution of molecular quantum energy states. The interface of these two materials is called a photovoltaic heterojunction. In traditional semiconductor theory, materials for forming PV heterojunctions have been denoted as generally being of either n or p type. Here n-type denotes that the majority carrier type is the electron. This could be viewed as the material having many electrons in relatively free energy states. The p-type denotes that the majority carrier type is the hole. Such material has many holes in relatively free energy states. The type of the background, i.e., not photo-generated, majority carrier concentration depends primarily on unintentional doping by defects or impurities. The type and concentration of impurities determine the value of the Fermi energy, or level, within the gap between the highest occupied molecular orbital (HOMO) energy level and the lowest unoccupied molecular orbital (LUMO) energy level, called the HOMO-LUMO gap. The Fermi energy characterizes the statistical occupation of molecular quantum energy states denoted by the value of energy for which the probability of occupation is equal to ½. A Fermi energy near the LUMO energy level indicates that electrons are the predominant carrier. A Fermi energy near the HOMO energy level indicates that holes are the predominant carrier. Accordingly, the Fermi energy is a primary characterizing property of traditional semiconductors and the prototypical PV heterojunction has traditionally been the p-n interface.

The term "rectifying" denotes, inter alia, that an interface has an asymmetric conduction characteristic, i.e., the interface supports electronic charge transport preferably in one direction. Rectification is associated normally with a built-in electric field which occurs at the heterojunction between appropriately selected materials.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

In the context of organic materials, the terms "donor" and "acceptor" refer to the relative positions of the HOMO and LUMO energy levels of two contacting but different organic materials. This is in contrast to the use of these terms in the inorganic context, where "donor" and "acceptor" may refer to types of dopants that may be used to create inorganic n– and p– types layers, respectively. In the organic context, if the LUMO energy level of one material in contact with another is lower, then that material is an acceptor. Otherwise it is a donor. It is energetically favorable, in the absence of an external bias, for electrons at a donor-acceptor junction to move into the acceptor material, and for holes to move into the donor material.

A significant property in organic semiconductors is carrier mobility. Mobility measures the ease with which a charge carrier can move through a conducting material in response to an electric field. In the context of organic photosensitive devices, a layer including a material that conducts preferentially by electrons due to a high electron mobility may be referred to as an electron transport layer, or ETL. A layer including a material that conducts preferentially by holes due to a high hole mobility may be referred to as a hole transport layer, or HTL. In one embodiment, an acceptor material is an ETL and a donor material is a HTL.

Conventional inorganic semiconductor PV cells employ a p-n junction to establish an internal field. Early organic thin film cell, such as reported by Tang, *Appl. Phys Lett.* 48, 183 (1986), contain a heterojunction analogous to that employed in a conventional inorganic PV cell. However, it is now recognized that in addition to the establishment of a p-n type junction, the energy level offset of the heterojunction also plays an important role.

The energy level offset at the organic D-A heterojunction is believed to be important to the operation of organic PV devices due to the fundamental nature of the photogeneration process in organic materials. Upon optical excitation of an organic material, localized Frenkel or charge-transfer excitons are generated. For electrical detection or current generation to occur, the bound excitons must be dissociated into their constituent electrons and holes. Such a process can be induced by the built-in electric field, but the efficiency at the electric fields typically found in organic devices ($F \sim 10^6$ V/cm) is low. The most efficient exciton dissociation in organic materials occurs at a donor-acceptor (D-A) interface. At such an interface, the donor material with a low ionization potential forms a heterojunction with an acceptor material with a high electron affinity. Depending on the alignment of the energy levels of the donor and acceptor materials, the dissociation of the exciton can become energetically favorable at such an interface, leading to a free electron polaron in the acceptor material and a free hole polaron in the donor material.

Organic PV cells have many potential advantages when compared to traditional silicon-based devices. Organic PV cells are light weight, economical in materials use, and can be deposited on low cost substrates, such as flexible plastic foils. However, organic PV devices typically have relatively low external quantum efficiency (electromagnetic radiation to electricity conversion efficiency), being on the order of 1% or less. This is, in part, thought to be due to the second order nature of the intrinsic photoconductive process. That is, carrier generation requires exciton generation, diffusion and ionization or collection. There is an efficiency η associated with each of these processes. Subscripts may be used as follows: P for power efficiency, EXT for external quantum efficiency, A for photon absorption exciton generation, ED for diffusion, CC for collection, and INT for internal quantum efficiency. Using this notation:

$$\eta_P \sim \eta_{EXT} = \eta_A * \eta_{ED} * \eta_{CC}$$

$$\eta_{EXT} = \eta_A * \eta_{INT}$$

The diffusion length ($L_D$) of an exciton is typically much less ($L_D \sim 50 \text{Å}$) than the optical absorption length ($\sim 500 \text{Å}$), requiring a trade off between using a thick, and therefore resistive, cell with multiple or highly folded interfaces, or a thin cell with a low optical absorption efficiency.

Typically, when light is absorbed to form an exciton in an organic thin film, a singlet exciton is formed. By the mechanism of intersystem crossing, the singlet exciton may decay to a triplet exciton. In this process energy is lost which will result in a lower efficiency for the device. If not for the energy loss from intersystem crossing, it would be desirable to use materials that generate triplet excitons, as triplet excitons generally have a longer lifetime, and therefore a longer diffusion length, than do singlet excitons.

Through the use of an organometallic material in the photoactive region, the devices described herein may efficiently utilize triplet excitons. We have found that the singlet-triplet mixing may be so strong for some organometallic compounds, like squaraines, that the absorptions involve excitation from the singlet ground states directly to the triplet excited states, eliminating the losses associated with conversion from the singlet excited state to the triplet excited state. The longer lifetime and diffusion length of triplet excitons in comparison to singlet excitons may allow for the use of a thicker photoactive region, as the triplet excitons may diffuse a greater distance to reach the donor-acceptor heterojunction, without sacrificing device efficiency. Accordingly, there remains a need to further develop photosensitive devices comprising certain squaraines, including symmetric and asymmetric arylsquaraines.

SUMMARY OF INVENTION

Described herein are novel squaraine compounds. In some embodiments, the squaraine compounds are aryl squaraines.

In one embodiment, the squaraine is a compound of formula I:

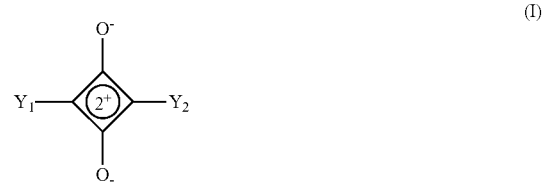

wherein:

$Y_1$ and $Y_2$ are independently selected from an optionally substituted amino group and an optionally substituted aryl group.

In one embodiment, the squaraine compound of Formula I is asymmetric, i.e., $Y_1$ and $Y_2$ are different.

Also described are organic photosensitive optoelectronic devices comprising at least one organic heterojunction formed from at least one squaraine compound of formula (I).

Further described herein are methods of preparing organic photosensitive optoelectronic devices. In some embodiments, the method comprises forming at least one donor-acceptor heterojunction comprising at least one compound of formula (I).

The foregoing and other features of the present disclosure will be more readily apparent from the following detailed description of exemplary embodiments, taken in conjunction with the attached drawings. It will be noted that for convenience all illustrations of devices show the height dimension exaggerated in relation to the width.

DETAILED DESCRIPTION OF THE INVENTION

Figure 1:
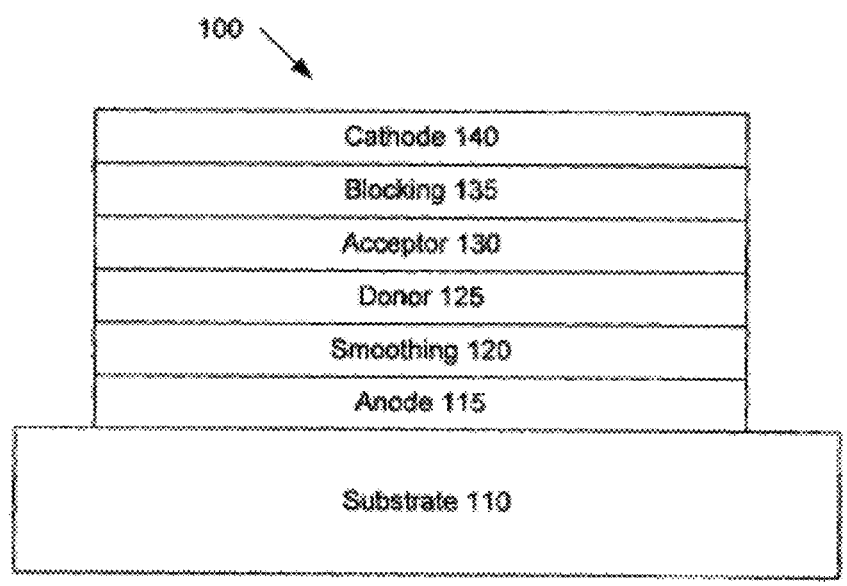
FIG. 1 illustrates an exemplary organic PV device comprising an anode, an anode smoothing layer, a donor layer, an acceptor layer, a blocking layer, and a cathode.
Figure 2:
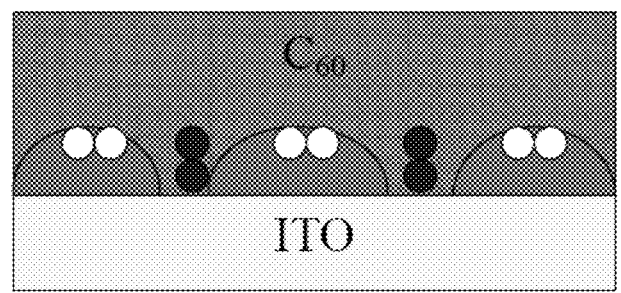
FIG. 2 illustrates an exemplary model of charge carrier separation in an exemplary SQ device, bounded excitons (white) in SQ phase and bounded excitons (black) in $C_{60}$ Phase.
Figure 3:
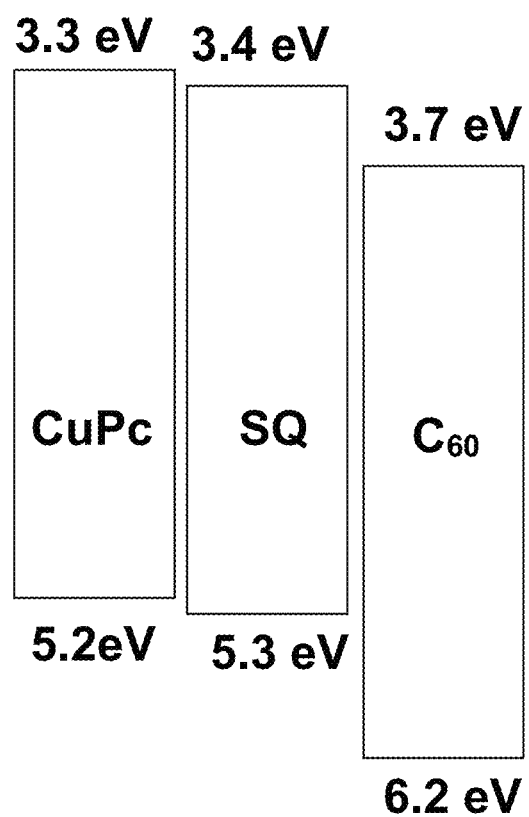
FIG. 3 is a schematic energy level diagram for devices with (a) CuPc or (b) SQ as the donor layer. The HOMO energies are from UPS. The LUMO energies are from IPES measurements, except for SQ where the LUMO and HOMO energies are determined by electrochemistry.

As used in the present disclosure, the following words, phrases, and symbols are generally intended to have the meanings set forth below, except to the extent in which they are used indicates otherwise. The following abbreviations and terms have the indicated meanings throughout:

A dash ("-") that is not between two letters or symbols is used to indicate a point of attachment for a substituent. For example, —CONH$_2$ is attached through the carbon atom.

"Alkyl" by itself or as part of another substituent refers to a saturated or unsaturated, branched, or straight-chain monovalent hydrocarbon radical derived by the removal of one hydrogen atom from a single carbon atom of a parent alkane, alkene, or alkyne. Examples of alkyl groups include, but are not limited to, methyl; ethyls such as ethenyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having mixtures of single, double, and triple carbon-carbon bonds. Where a specific level of saturation is intended, the terms "alkanyl," "alkenyl," and "alkynyl" are used. In certain embodiments, an alkyl group comprises from 1 to 20 carbon atoms, in certain embodiments, from 1 to 10 carbon atoms, in certain embodiments, from 1 to 8 or 1 to 6 carbon atoms, and in certain embodiments from 1 to 3 carbon atoms.

"Amino" refers to the radical —NH$_2$.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes 5- and 6-membered carbocyclic aromatic rings fused to a 5- to 7-membered heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octacene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can comprise from 5 to 20 carbon atoms, and in certain embodiments, from 5 to 12 carbon atoms. Aryl, however, does not encompass or overlap in any way with heteroaryl, separately defined herein. Hence, a multiple ring system in which one or more carbocyclic aromatic rings is fused to a heterocycloalkyl aromatic ring, is heteroaryl, not aryl, as defined herein.

"Carbocyclyl" is intended to include both "aryl" and "cycloalkyl" groups.

"Compounds" refers to compounds encompassed by structural formula (I) herein and includes any specific compounds within this formula whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan.

For the purposes of the present disclosure, "chiral compounds" are compounds having at least one center of chirality (i.e. at least one asymmetric atom, in particular at least one asymmetric C atom), having an axis of chirality, a plane of chirality or a screw structure. "Achiral compounds" are compounds which are not chiral.

Compounds of formula (I) include, but are not limited to, optical isomers of compounds of formula (I), racemates thereof, and other mixtures thereof. In such embodiments, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. However, unless otherwise stated, it should be assumed that formula (I) covers all asymmetric variants of the compounds described herein, including isomers, racemates, enantiomers, diastereomers, and other mixtures thereof. In addition, compounds of formula (I) include Z- and E-forms (e.g., cisand trans-forms) of compounds with double bonds. In embodiments in which compounds of Formulas I and IA exist in various tautomeric forms, compounds provided by the present disclosure include all tautomeric forms of the compound.

The compounds of formula (I) may also exist in several tautomeric forms including the enol form, the keto form, and mixtures thereof. Accordingly, the chemical structures depicted herein encompass all possible tautomeric forms of the illustrated compounds. Compounds may exist in unsolvated forms as well as solvated forms, including hydrated forms and as N-oxides. In general, compounds may be hydrated, solvated, or N-oxides. Certain compounds may exist in single or multiple crystalline or amorphous forms. In general, all physical forms are equivalent for the uses contemplated herein and are intended to be within the scope provided by the present disclosure. Further, when partial structures of the compounds are illustrated, an asterisk ( ) indicates the point of attachment of the partial structure to the rest of the molecule.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, and in certain embodiments, $C_{3-12}$ cycloalkyl or $C_{5-12}$ cycloalkyl.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one aromatic ring fused to at least one other ring, which can be aromatic or non-aromatic in which at least one ring atom is a heteroatom. Heteroaryl encompasses 5- to 12-membered aromatic, such as 5- to 7-membered, monocyclic rings containing one or more, for example, from 1 to 4, or in certain embodiments, from 1 to 3, heteroatoms chosen from N, O, and S, with the remaining ring atoms being carbon; and bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. In certain embodiments, when the total number of N, S, and O atoms in the heteroaryl group exceeds one, the heteroatoms are not adjacent to one another. In certain embodiments, the total number of N, S, and O atoms in the heteroaryl group is not more than two. In certain embodiments, the total number of N, S, and O atoms in the aromatic heterocycle is not more than one. Heteroaryl does not encompass or overlap with aryl as defined herein.

Examples of heteroaryl groups include, but are not limited to, groups derived from acridine, arsindole, carbazole, ÿ-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is from 5- to 20-membered heteroaryl, and in certain embodiments from 5- to 12-membered heteroaryl or from 5- to 10-membered heteroaryl. In certain embodiments heteroaryl groups are those derived from thiophene, pyrrole, benzothiophene, benzofuran, indole, pyridine, quinoline, imidazole, oxazole, and pyrazine.

"Heterocyclyl" by itself or as part of another substituent refers to a partially saturated or unsaturated cyclic alkyl radical in which one or more carbon atoms (and any associated hydrogen atoms) are independently replaced with the same or different heteroatom. Examples of heteroatoms to replace the carbon atom(s) include, but are not limited to, N, P, O, S, Si, etc. Where a specific level of saturation is intended, the nomenclature "heterocycloalkanyl" or "heterocycloalkenyl" is used. Examples of heterocycloalkyl groups include, but are not limited to, groups derived from epoxides, azirines, thiiranes, imidazolidine, morpholine, piperazine, piperidine, pyrazolidine, pyrrolidine, quinuclidine, and the like.

"Substituted" refers to a group in which one or more hydrogen atoms are independently replaced with the same or different substituent(s). Examples of substituents include, but are not limited to, —$R^{64}$, —$R^{60}$, —O—, (—OH), =O, —$OR^{60}$, —$SR^{60}$, —S—, =S, —$NR^{60}R^{61}$, =$NR^{60}$, —$CX_3$, —CN, —$CF_3$, —OCN, —SCN, —NO, —$NO_2$, =$N_2$, —$N_3$, —$S(O)_2O$—, —$S(O)_2OH$, —$S(O)_2R^{60}$, —$OS(O_2)O$—, —$OS(O)_2R^{60}$, —P(O)(O—)$_2$, —P(O)($OR^{60}$)(O—), —OP(O)($OR^{60}$)($OR^{61}$), —C(O)$R^{60}$, —C(S)$R^{60}$, —C(O)$OR^{60}$, —C(O)$NR^{60}R^{61}$, —C(O)O—, —C(S)$OR^{60}$, —$NR^{62}C(O)NR^{60}R^{61}$, —$NR^{62}C(S)NR^{60}R^{61}$, —$NR^{62}C(NR^{63})NR^{60}R^{61}$, —C($NR^{62}$)$NR^{60}R^{61}$, —$S(O)_2$, $NR^{60}R^{61}$, —$NR^{63}S(O)_2R^{60}$, —$NR^{63}C(O)R^{60}$, and —$S(O)R^{60}$ where each —$R^{64}$ is independently a halogen; each $R^{60}$ and $R^{61}$ are independently hydrogen, alkyl, substituted alkyl, alkoxy, substituted alkoxy, cycloalkyl, substituted cycloalkyl, heterocycloalkyl, substituted heterocycloalkyl, aryl, substituted aryl, heteroaryl, substituted heteroaryl, arylalkyl, substituted arylalkyl, heteroarylalkyl, or substituted heteroarylalkyl, or $R^{60}$ and $R^{61}$ together with the nitrogen atom to which they are bonded to form a heterocyclyl, substituted heterocyclyl, heteroaryl, or substituted heteroaryl ring, and $R^{62}$ and $R^{63}$ are independently hydrogen, alkyl, substituted alkyl, aryl, substituted aryl, arylalkyl, substituted arylalkyl, cycloalkyl, substituted cycloalkyl, heterocyclyl, substituted heterocyclyl, heteroaryl, substituted heteroaryl, or heteroarylalkyl, or $R^{62}$ and $R^{63}$ together with the atom to which they are bonded form one or more heterocyclyl, substituted heterocyclyl, heteroaryl, or substituted heteroaryl rings. In certain embodiments, a tertiary amine or aromatic nitrogen may be substituted with one or more oxygen atoms to form the corresponding nitrogen oxide.

As used in this specification and the appended claims, the articles "a," "an," and "the" include plural referents unless expressly and unequivocally limited to one referent.

All numerical ranges herein include all numerical values and ranges of all numerical values within the recited range of numerical values. Further, while the numerical ranges and parameters setting forth the broad scope of the disclosure are approximations as discussed above, the numerical values set forth in the Examples section are reported as precisely as possible. It should be understood, however, that such numerical values inherently contain certain errors resulting from the measurement equipment and/or measurement technique.

In some embodiments, the compounds described herein may comprise squaraine compounds represented by the following graphic formula (I):

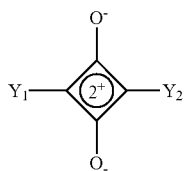

(I)

wherein, $Y_1$ and $Y_2$ are independently selected from an optionally substituted amino group or an optionally substituted aryl group.

In some embodiments, the compounds are asymmetric, i.e., $Y_1$ and $Y_2$ are different.

In some embodiments, $Y_1$ and $Y_2$ are independently selected from $—NR_3R_4$ and a group of formula II:

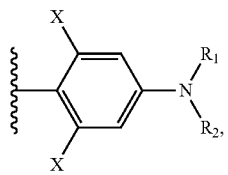

(II)

wherein X for each occurrence is independently selected from hydrogen and hydroxyl;

$R_1$ and $R_2$ for each occurrence are independently selected from optionally substituted alkyl, optionally substituted aryl, and optionally substituted heteroaryl, or $R_1$ and $R_2$ are taken together with any intervening atoms to form a group selected from optionally substituted heteroaryl and optionally substituted heterocyclyl; and $R_3$ and $R_4$ for each occurrence are independently selected from optionally substituted alkyl, optionally substituted aryl, and optionally substituted heteroaryl, or $R_3$ and $R_4$ are taken together with any intervening atoms to form a group selected from optionally substituted heteroaryl and optionally substituted heterocyclyl.

In some embodiments, said optionally substituted heteroaryl and the optionally substituted heterocyclyl are independently selected from monocyclic and multicyclic groups. In some embodiments, the multicyclic group comprises two or more fused rings. In some embodiments, at least one of $R_3$ and $R_4$ comprise an aryl group.

As used herein, amino and substituted amino groups are intended to include any salts, such as acid addition salts, thereof. For example, any reference to an amine also contemplates the ammonium salt and any reference to or embodiment of the group $NR^1R^2$ should be construed to include analogous salts such as acid addition salts, etc.

In yet another embodiment, a compound of formula (I) is selected, with the proviso that when at least one of $Y_1$ and $Y_2$ comprises the group of formula (II), $R_1$ and $R_2$ are taken together with any intervening atoms to form a group selected from optionally substituted heteroaryl and optionally substituted heterocyclyl.

In some embodiments, the group of formula (II) is chosen from the group of formula (III):

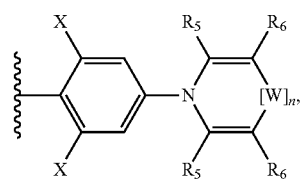

(III)

wherein

W is selected from S, O, Se, and Te;

n is an integer selected from 0 and 1; and $R_5$ and $R_6$ for each occurrence are independently selected from optionally substituted amino, cyano, halo, mercapto, optionally substituted alkenyl, optionally substituted alkynyl, optionally substituted alkyl, optionally substituted aryl, and optionally substituted heteroaryl, optionally substituted heterocyclyl, and optionally substituted carbocyclyl, or $R_5$ and $R_6$ attached to adjacent atoms are taken together with any intervening atoms to form a group selected from optionally substituted aryl, optionally substituted heteroaryl, optionally substituted carbocyclyl, and optionally substituted heterocyclyl.

In another embodiment, a compound of formula (I) is selected, wherein $Y_1$ comprises $—NR_3R_4$; and $Y_2$ comprises

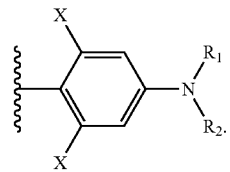

In some embodiments, at least one of $Y_1$ and $Y_2$ comprises

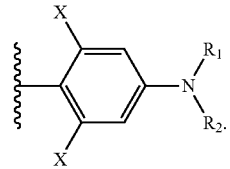

In some embodiments, at least one X comprises hydroxyl.

In some embodiments, at least one of $Y_1$ and $Y_2$ comprises $—NR_3R_4$.

In still another embodiment, a compound of formula (I) is selected, wherein $Y_1$ is $—NR_3R_4$ and $Y_2$ is optionally substituted aryl, wherein $R_3$ and $R_4$ are independently selected from optionally substituted alkyl, optionally substituted aryl, and optionally substituted heteroaryl, or $R_3$ and $R_4$ are taken together with any intervening atoms to form a group selected from optionally substituted heteroaryl and optionally substituted heterocyclyl.

In some embodiments, $Y_1$ comprises an optionally substituted aryl, and $Y_2$ is

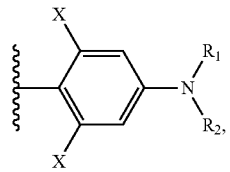

wherein

X for each occurrence is independently selected from hydrogen and hydroxyl; and $R_1$ and $R_2$ for each occurrence are independently selected from optionally substituted alkyl, optionally substituted aryl, and optionally substituted heteroaryl, or $R_1$ and $R_2$ are taken together with any intervening atoms to form a group selected from optionally substituted heteroaryl and optionally substituted heterocyclyl.

It is appreciated that the squaraine compound of formula I may or may not be symmetric. As used herein, the term "symmetric" is intended to include compounds with a point group symmetry of an order higher than the $C_s$ symmetry group.

In some embodiments, the compound of formula (I) is amorphous.

In some embodiments, the compound of formula (I) is selected from 2,4-bis[4-N-carbazolo-2,6-dihydroxyphenyl] squaraine (CBZSQ), 2,4-bis[4-N-phenothiazino-2,6-dihydroxyphenyl] squaraine (PTSQ), 2,4-bis[4-(N,N-diphenylamino)-2,6-dihydroxyphenyl] squaraine (DPSQ), 2,4-bis[4-(N-Phenyl-1-naphthylamino)-2,6-dihydroxyphenyl] squaraine (1NPSQ), 2,4-bis[4-(N-Phenyl-2-naphthylamino)-2,6-dihydroxyphenyl] squaraine (2NPSQ), {2-[4-(N,N-diisobutylamino)-2,6-dihydroxyphenyl]-4-diphenylamino} squaraine (USSQ), {2-[4-(N,N-diphenylamino)-2,6-dihydroxyphenyl]-4-diphenylamino} squaraine (DPUSQ), and diphenylamino-squarate (YSQ).

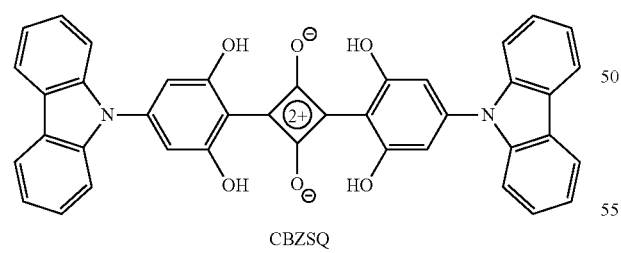

CBZSQ

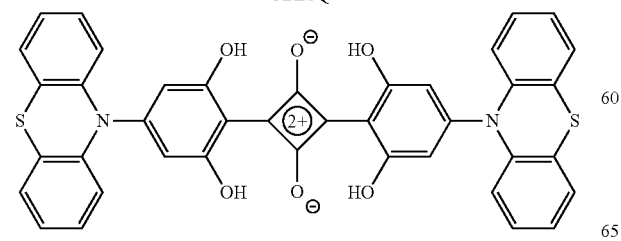

PTSQ

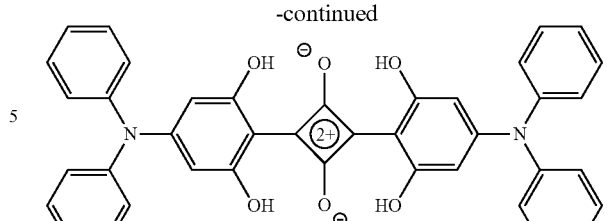

DPSQ

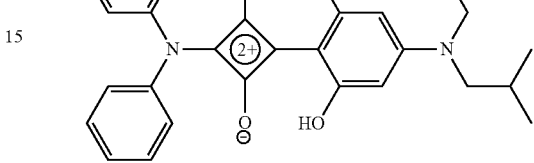

USSQ

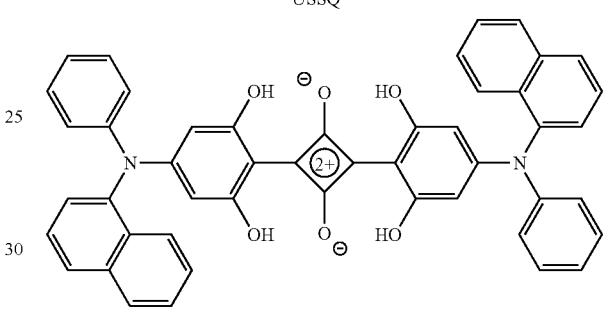

1NPSQ

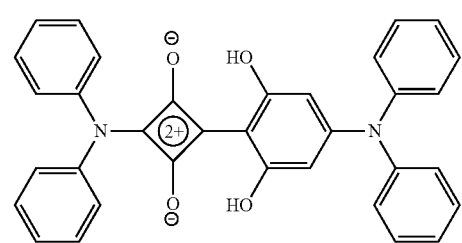

DPUSQ

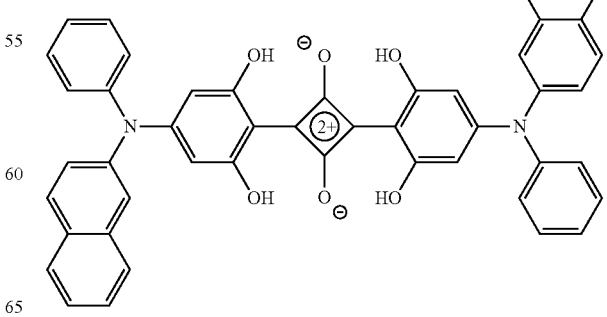

2NPSQ

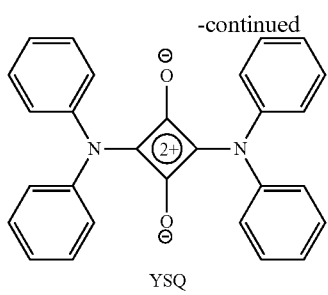

YSQ

In all of the foregoing examples, the compounds described herein may be useful alone, as mixtures, or in combination with other compounds, compositions, and/or materials.

Methods for obtaining the novel compounds described herein will be evident to those of ordinary skill in the art, suitable procedures being described, for example, in the reaction schemes and examples below.

Scheme 1

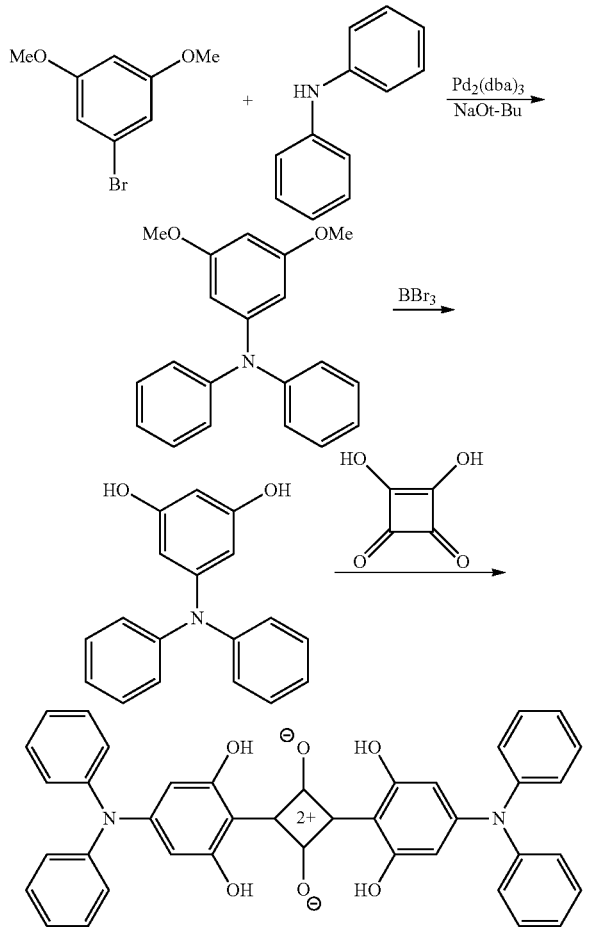

Scheme 1 depicts a method of preparing symmetric aryl squaraines in two steps. The aryl aniline was synthesized by Buchwald reaction with yields of about 90% of the desired diaryl amine. Exemplary reactions are described in Son et al., *Poly. Sci. Part A: Polym. Chem.*, 48: 635 (2009). The methoxy groups of the intermediate were deprotected using BBr$_3$ to provide the corresponding hydroxyl-substituted arylaniline. The arylaniline is then reacted with squaric acid under N$_2$ overnight to yield the crude product, which was purified by recrystallization twice from DCM and methanol to provide the desired squaraine product in about 50% yield.

Scheme 2

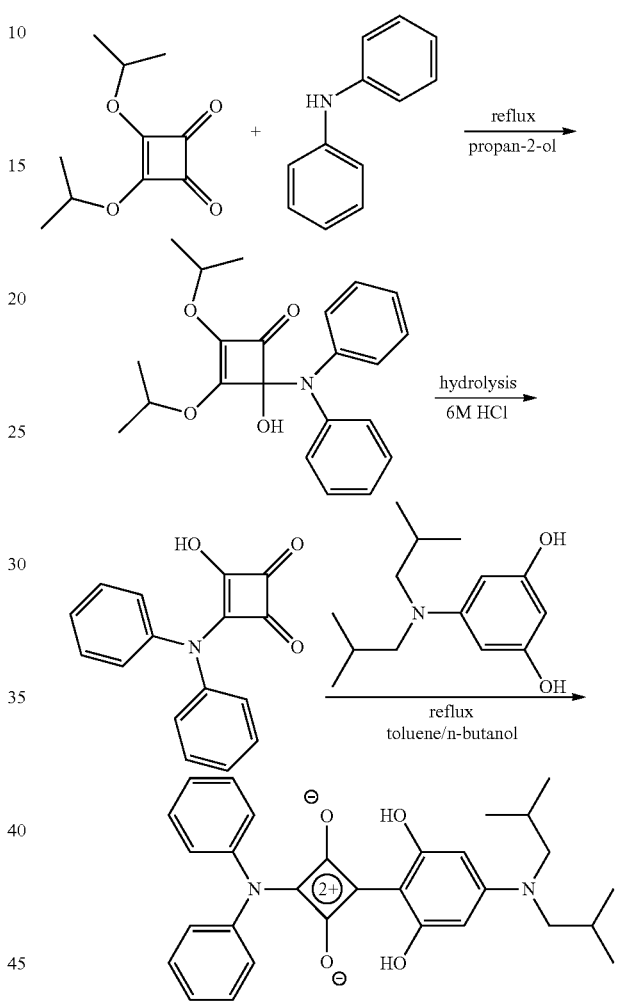

Scheme 2 depicts a method of preparing unsymmetrical aryl-amino squaraines. Diarylaminosquarate was first synthesized by reacting 3,4-disopropoxycyclobut-3-ene-1,2-dione with diarylamine in propan-2-ol, followed by hydrolysis of the intermediate with HCl. The diarylaminosquarate is then reacted with a hydroxyl-substituted arylamine to yield the resulting squaraine.

Scheme 3

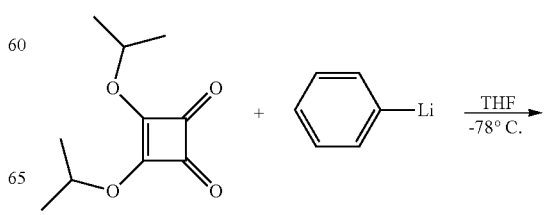

-continued

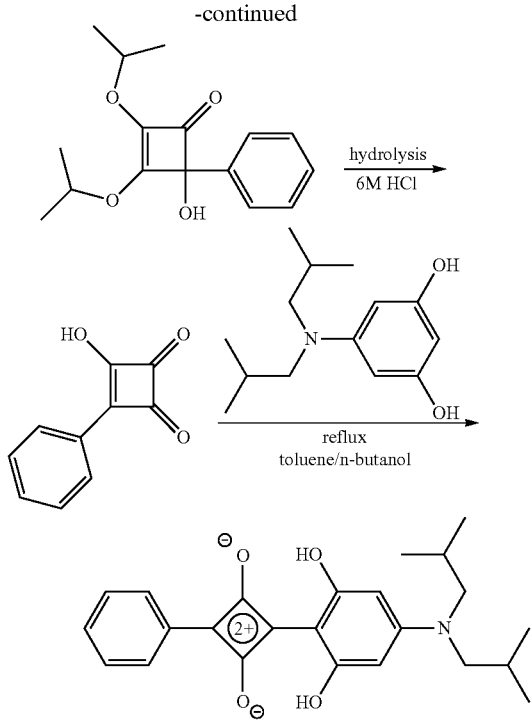

Scheme 3 depicts a method of preparing asymmetric aryl squaraines, 3,4-disopropoxycyclobut-3-ene-1,2-dione is reacted with the aryllithium compound in THF at −78° C. After quenching the mixture with water, the arylsquarate intermediate is extracted with DCM, and subsequently hydrolyzed with HCl to form the arylsquarate. The asymmetric diarylsquaraine product is obtained by reacting the arylsquarate intermediate with the desired hydroxyl-substituted arylamine.

In some embodiments, the squaraine compounds described herein may be used in the preparation of organic photosensitive optoelectronic devices. In some embodiments, the organic photosensitive optoelectronic devices described herein have at least one donor-acceptor heterojunction comprising at least one compound of formula (I):

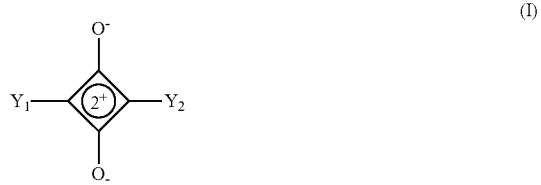

(I)

wherein:
$Y_1$ and $Y_2$ are independently selected from an optionally substituted amino group and an optionally substituted aryl group.

In one embodiment, the squaraine is asymmetric, i.e, $Y_1$ and $Y_2$ are different.

The organic optoelectronic devices of the embodiments of described herein may be used, for example, to generate a usable electrical current from incident electromagnetic radiation (e.g., PV devices) or may be used to detect incident electromagnetic radiation. In some embodiments, the devices described herein may be prepared by forming a photoactive region comprising at least one donor-acceptor heterojunction having at least one compound of formula (I). The photoactive region is the portion of the photosensitive device that absorbs electromagnetic radiation to generate excitons that may dissociate in order to generate an electrical current. In some embodiments, the device is a solar cell and the donor-acceptor heterojunction is formed at an interface of a donor material comprising at least one compound of formula (I) and an acceptor material.

Embodiments of the devices described herein may comprise an anode, a cathode, and a photoactive region between the anode and the cathode. Organic photosensitive optoelectronic devices may also include at least one transparent electrode to allow incident radiation to be absorbed by the device. Several PV device materials and configurations are described in the following U.S. Pat. Nos. 6,657,378; 6,580,027; and 6,352,777, all three of which are incorporated herein by reference in their entirety.

FIG. 1 shows an organic photosensitive optoelectronic device 100. The figures are not necessarily drawn to scale. Device 100 may include a substrate 110, an anode 115, an anode smoothing layer 120, a donor layer 125, an acceptor layer 130, a blocking layer 135, and a cathode 140. Cathode 140 may be a compound cathode having a first conductive layer and a second conductive layer. Device 100 may be fabricated by depositing the layers described, in order. Charge separation may occur predominantly at the organic heterojunction between donor layer 125 and acceptor layer 130. The built-in potential at the heterojunction is determined by the HOMO-LUMO energy level difference between the two materials contacting to form the heterojunction. The HOMO-LUMO gap offset between the donor and acceptor materials produces an electric field at the donor/acceptor interface that facilitates charge separation for excitons created within an exciton diffusion length of the interface.

The specific arrangement of layers illustrated in FIG. 1 is exemplary only, and is not intended to be limiting. For example, some of the layers (such as blocking layers) may be omitted. Other layers (such as reflective layers or additional acceptor and donor layers) may be added. The order of layers may be altered. Arrangements other than those specifically described may be used.

The substrate may be any suitable substrate that provides desired structural properties. The substrate may be flexible or rigid, planar or non-planar. The substrate may be transparent, translucent or opaque. Plastic and glass are examples of rigid substrate materials that may be used herein. Plastic and metal foils are examples of flexible substrate materials that may be used according to the present disclosure. The material and thickness of the substrate may be chosen to obtain desired structural and optical properties.

U.S. Pat. No. 6,352,777, incorporated herein by reference, provides examples of electrodes, or contacts, that may be used in a photosensitive optoelectronic device. When used herein, the terms "electrode" and "contact" refer to layers that provide a medium for delivering photo-generated current to an external circuit or providing a bias voltage to the device. That is, an electrode, or contact, provides the interface between the active regions of an organic photosensitive optoelectronic device and a wire, lead, trace or other means for transporting the charge carriers to or from the external circuit.

In a photosensitive optoelectronic device, it is desirable to allow the maximum amount of ambient electromagnetic radiation from the device exterior to be admitted to the photoconductively active interior region. That is, the electromagnetic radiation must reach a photoconductive layer(s), where it can be converted to electricity by photoconductive absorption. This often dictates that at least one of the electrical contacts should be minimally absorbing and minimally reflecting of the incident electromagnetic radiation. That is, such a contact should be substantially transparent. The opposing electrode may be a reflective material so that light which has passed through the cell without being absorbed is reflected back through the cell.

As used herein, a layer of material or a sequence of several layers of different materials is said to be "transparent" when the layer or layers permit at least 50% of the ambient electromagnetic radiation in relevant wavelengths to be transmitted through the layer or layers. Similarly, layers which permit some, but less that 50% transmission of ambient electromagnetic radiation in relevant wavelengths are said to be "semi-transparent."

As used herein, "top" means farthest away from the substrate, while "bottom" means closest to the substrate. For example, for a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

In one embodiment, the electrodes are composed of metals or "metal substitutes". Herein the term "metal" is used to embrace both materials composed of an elementally pure metal, e.g., Mg, Ag, Au, or Al, and also metal alloys which are materials composed of two or more elementally pure metals, e.g., Mg and Ag together, denoted Mg:Ag.

Here, the term "metal substitute" refers to a material that is not a metal within the normal definition, but which has the metal-like properties that are desired in certain appropriate applications. Commonly used metal substitutes for electrodes and charge transfer layers would include doped wide-bandgap semiconductors, for example, transparent conducting oxides. Transparent conductive polymers may also be used. Non-limiting transparent conducting oxides include indium tin oxide (ITO), tin oxide (TO), gallium indium tin oxide (GITO), zinc oxide (ZO), and zinc indium tin oxide (ZITO), glass and transparent conductive polymers. Exemplary transparent conductive polymers include, for example, polyaniline (PANI).

ITO is a highly doped degenerate n+ semiconductor with an optical bandgap of approximately 3.2 eV, rendering it transparent to wavelengths greater than approximately 390 nm. Another suitable metal substitute is the transparent conductive polymer polyaniline (PANI) and its chemical relatives. Metal substitutes may be further selected from a wide range of non-metallic materials, wherein the term "non-metallic" is meant to embrace a wide range of materials provided that the material is free of metal in its chemically uncombined form. When a metal is present in its chemically uncombined form, either alone or in combination with one or more other metals as an alloy, the metal may alternatively be referred to as being present in its metallic form or as being a "free metal". Thus, the metal substitute electrodes of the present invention may sometimes be referred to as "metal-free" wherein the term "metal-free" is expressly meant to embrace a material free of metal in its chemically uncombined form.

Free metals typically have a form of metallic bonding that results from a sea of valence electrons which are free to move in an electronic conduction band throughout the metal lattice. While metal substitutes may contain metal constituents they are "non-metallic" on several bases. They are not pure free-metals nor are they alloys of free-metals. When metals are present in their metallic form, the electronic conduction band tends to provide, among other metallic properties, a high electrical conductivity as well as a high reflectivity for optical radiation.

Embodiments of the present disclosure may include, as one or more of the transparent electrodes of the photosensitive optoelectronic device, a highly transparent, non-metallic, low resistance cathode such as disclosed in U.S. Pat. No. 6,420,031, to Parthasarathy et al. ("Parthasarathy '031"), or a highly efficient, low resistance metallic/non-metallic compound cathode such as disclosed in U.S. Pat. No. 5,703,436 to Forrest et al. ("Forrest '436"), both incorporated herein by reference in their entirety. Each type of cathode may be prepared in a fabrication process that includes sputter depositing an ITO layer onto either an organic material, such as copper phthalocyanine (CuPc), to form a highly transparent, non-metallic, low resistance cathode or onto a thin Mg:Ag layer to form a highly efficient, low resistance metallic/non-metallic compound cathode. Parthasarathy '031 discloses that an ITO layer onto which an organic layer had been deposited, instead of an organic layer onto which the ITO layer had been deposited, does not function as an efficient cathode. For PVs the ITO would be deposited onto the substrate, unless the layers were being deposited in the reverse orientation.

In addition to CuPc, an organic compound that facilitates the formation of crystalline or amorphous films (such as, e.g., NPD) may be utilized as a hole transporting material between the anode (e.g., ITO) and the squaraine. The organic film-facilitating compound does not contribute to photon absorption and has suitable energetics with squaraines such as SQ. When used in concert with $C_{60}$, the presence of a layer of an organic film-facilitating compound may ensure that the $C_{60}$ is not be in contact with the ITO, thus preventing loss of $C_{60}$ inherent photocurrent. Additionally, an organic film-facilitating compound does not trap charge according to its well known good hole mobility.

Herein, the term "cathode" is used in the following manner. In a non-stacked PV device or a single unit of a stacked PV device under ambient irradiation and connected with a resistive load and with no externally applied voltage, e.g., a PV device, electrons move to the cathode from the photo-conducting material. Similarly, the term "anode" is used herein such that in a PV device under illumination, holes move to the anode from the photo-conducting material, which is equivalent to electrons moving in the opposite manner. It will be noted that as the terms are used herein, anodes and cathodes may be electrodes or charge transfer layers.

An organic photosensitive device will comprise at least one photoactive region in which light is absorbed to form an excited state, or "exciton", which may subsequently dissociate into an electron and a hole. The dissociation of the exciton will typically occur at the heterojunction formed by the juxtaposition of an acceptor layer and a donor layer. For example, in the device of FIG. 1, the "photoactive region" may include donor layer 125 and acceptor layer 130. In some embodiments, the donor layer may comprise at least one compound of formula (I):

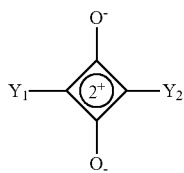
(I)

wherein:
(a) $Y_1$ and $Y_2$ are independently selected from a substituted amino group or a substituted aryl group, or
(b) $Y_1$ and $Y_2$ are independently selected from an optionally substituted amino group or an optionally substituted aryl group, wherein the squaraine compound is not symmetric.

In some embodiments, the organic photosensitive optoelectronic devices described herein may comprise at least two different squaraines to provide more efficient light harvesting at wavelengths ranging from 500 to 850 nm, when compared to a donor-acceptor heterojunction comprising, at most, one squaraine.

Such squaraine compounds may be used alone or in addition to other donor materials. All references to compounds of formula (I), including, for example, the devices and methods comprising compounds of formula (I) are intended to encompass any salts or derivatives of these compounds. For example, one of skill in the art will recognize that a compound of formula (I) may be present in a ketone or alcohol form rather than the charge separated form depicted.

The acceptor material may be comprised of, for example, perylenes, naphthalenes, fullerenes or nanotubules. Exemplary acceptor materials include $C_{60}$, $C_{70}$, $C_{84}$, 3,4,9,10-perylenetracarboxylic dianhydride (PTCDA), 3,4,9,10-perylenetracarboxylic diimide (PTCDI), 3,4,9,10-perylenetetracarboxylic-bis-benzimidazole (PTCBI), 1,4,5,8-naphthalenetetracarboxylic dianhydride (NTCDA), copper phthalocyanine (CuPc), and copper-hexadecafluoro-phthalocyanine ($F_{16}$—CuPc).

In one embodiment, the stacked organic layers include one or more exciton blocking layers (EBLs) as described in U.S. Pat. No. 6,097,147, Peumans et al, *Applied Physics Letters* 2000, 76, 2650-52, and co-pending application Ser. No. 09/449,801, filed Nov. 26, 1999, both incorporated herein by reference. Higher internal and external quantum efficiencies have been achieved by the inclusion of an EBL to confine photogenerated excitons to the region near the dissociating interface and to prevent parasitic exciton quenching at a photosensitive organic/electrode interface. In addition to limiting the volume over which excitons may diffuse, an EBL can also act as a diffusion barrier to substances introduced during deposition of the electrodes. In some circumstances, an EBL can be made thick enough to fill pinholes or shorting defects which could otherwise render an organic PV device non-functional. An EBL can therefore help protect fragile organic layers from damage produced when electrodes are deposited onto the organic materials. EBLs can also function as optical spacers that allow for the focusing of optical field peaks in the active area of the cell.

Exemplary electron or exciton blocking materials include, for example, bathocuproine (BCP), bathophenanthroline (BPhen), 3,4,9,10-perylenetetracarboxylicbis-benzimidazole (PTCBI), 1,3,5-tris(N-phenylbenzimidazol-2-yl)benzene (TPBi), tris(acetylacetonato) ruthenium(III) (RuAcaca$_3$), and aluminum(III)phenolate (Alq$_2$OPH). In some embodiments, the EBL is situated between the acceptor layer and the cathode.

It is believed that the EBLs derive their exciton blocking property from having a LUMO-HOMO energy gap substantially larger than that of the adjacent organic semiconductor from which excitons are being blocked. Thus, the confined excitons are prohibited from existing in the EBL due to energy considerations. While it is desirable for the EBL to block excitons, it is not desirable for the EBL to block all charge. However, due to the nature of the adjacent energy levels, an EBL may block one sign of charge carrier. By design, an EBL will exist between two other layers, usually an organic photosensitive semiconductor layer and an electrode or charge transfer layer or charge recombination layers. The adjacent electrode or charge transfer layer will be in context either a cathode or an anode. Therefore, the material for an EBL in a given position in a device will be chosen so that the desired sign of carrier will not be impeded in its transport to or from the electrode or charge transfer layer. Proper energy level alignment ensures that no barrier to charge transport exists, preventing an increase in series resistance. For example, it is desirable for a material used as a cathode side EBL to have a LUMO energy level closely matching the LUMO energy level of the adjacent ETL material so that any undesired barrier to electrons is minimized.

It should be appreciated that the exciton blocking nature of a material is not an intrinsic property of its HOMO-LUMO energy gap. Whether a given material will act as an exciton blocker depends upon the relative HOMO and LUMO energy levels of the adjacent organic photosensitive material. Therefore, it is not possible to identify a class of compounds in isolation as exciton blockers without regard to the device context in which they may be used. However, with the teachings herein one of ordinary skill in the art may identify whether a given material will function as an exciton blocking layer when used with a selected set of materials to construct an organic PV device.

Optionally, the EBL layer may be doped with a suitable dopant, including but not limited to 3,4,9,10-perylenetracarboxylic dianhydride (PTCDA), 3,4,9,10-perylenetracarboxylic diimide (PTCDI), 3,4,9,10-perylenetetracarboxylic-bis-benzimidazole (PTCBI), 1,4,5,8-naphthalenetetracarboxylic dianhydride (NTCDA), and derivatives thereof. It is thought that the BCP as deposited in the present devices is amorphous. The present apparently amorphous BCP exciton blocking layers may exhibit film recrystallization, which is especially rapid under high light intensities. The resulting morphology change to polycrystalline material results in a lower quality film with possible defects such as shorts, voids or intrusion of electrode material.

Accordingly, it has been found that doping of some EBL materials, such as BCP, that exhibit this effect with a suitable, relatively large and stable molecule can stabilize the EBL structure to prevent performance degrading morphology changes. It should be further appreciated that doping of an EBL which is transporting electrons in a given device with a material having a LUMO energy level close to that of the EBL will help insure that electron traps are not formed which might produce space charge build-up and reduce performance. Additionally, it should be appreciated that relatively low doping densities should minimize exciton generation at isolated dopant sites. Since such excitons are effectively prohibited from diffusing by the surrounding EBL material, such absorptions reduce device photoconversion efficiency.

Representative embodiments may also comprise transparent charge transfer layers or charge recombination layers. As described herein, "charge transfer layers" are distinguished from acceptor and donor layers by the fact that charge transfer layers are frequently, but not necessarily, inorganic (often metals) and they may be chosen not to be photoconductively active. The term "charge transfer layer" is used herein to refer to layers similar to but different from electrodes in that a charge transfer layer only delivers charge carriers from one subsection of an optoelectronic device to the adjacent subsection.

The term "charge recombination layer" is used herein to refer to layers similar to but different from electrodes in that a charge recombination layer allows for the recombination of electrons and holes between adjacent charge carrier layers and may also enhance internal optical field strength near one or more active layers. A charge recombination layer can be constructed of semi-transparent metal nanoclusters, nanoparticle or nanorods as described in U.S. Pat. No. 6,657,378, incorporated herein by reference in its entirety.

In some embodiments, an anode-smoothing layer may be situated between the anode and the donor layer. One material for this layer comprises a film of 3,4-polyethylenedioxythiophene:polystyrenesulfonate (PEDOT:PSS). The introduction of the PEDOT:PSS layer between the anode (ITO) and the donor layer (CuPc) may lead to greatly improved fabrication yields. Without being bound by any particular theory, it is believed that the improved fabrication yields is a result of the ability of the spin-coated PEDOT:PSS film to planarize the ITO, whose rough surface could otherwise result in shorts through the thin molecular layers.

In a further embodiment, one or more of the layers may be treated with plasma prior to depositing the next layer. The layers may be treated, for example, with a mild argon or oxygen plasma. This treatment may help to reduce the series resistance. It is particularly advantageous that the PEDOT:PSS layer be subject to a mild plasma treatment prior to deposition of the next layer.

The simple layered structure illustrated in FIG. 1 is provided by way of non-limiting example, and it is understood that embodiments of the invention may be used in connection with a wide variety of other structures. The specific materials and structures described are exemplary in nature, and other materials and structures may be used. Functional organic photosensitive optoelectronic devices may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. Organic layers that are not a part of the photoactive region, i.e., organic layers that generally do not absorb photons that make a significant contribution to photocurrent, may be referred to as "non-photoactive layers." Examples of non-photoactive layers include EBLs and anode-smoothing layers. Other types of non-photoactive layers may also be used.

Non-limiting examples of organic materials for use in the photoactive layers of a photosensitive device include cyclo-metallated organometallic compounds. The term "organometallic" as used herein is as generally understood by one of ordinary skill in the art and as given, for example, in "Inorganic Chemistry" (2nd Edition) by Gary L. Miessler and Donald A. Tarr, Prentice Hall (1998). Thus, the term organometallic refers to compounds which have an organic group bonded to a metal through a carbon-metal bond. This class does not include per se coordination compounds, which are substances having only donor bonds from heteroatoms, such as metal complexes of amines, halides, pseudohalides (CN, etc.), and the like. In practice, organometallic compounds generally comprise, in addition to one or more carbon-metal bonds to an organic species, one or more donor bonds from a heteroatom. The carbon-metal bond to an organic species refers to a direct bond between a metal and a carbon atom of an organic group, such as phenyl, alkyl, alkenyl, etc., but does not refer to a metal bond to an "inorganic carbon," such as the carbon of CN or CO. The term cyclometallated refers to compounds that comprise an bidentate organometallic ligand so that, upon bonding to a metal, a ring structure is formed that includes the metal as one of the ring members.

Organic layers may be fabricated using vacuum deposition, spin coating, organic vapor-phase deposition, inkjet printing and other methods known in the art. In some embodiments, the donor-acceptor heterojunction is disposed over a substrate. The organic photosensitive optoelectronic device described herein may be prepared, for example, by depositing the at least one compound of formula (I) by one or more processes chosen from vacuum deposition and solution processing. Solution processing may comprise one or more technique chosen from spin coating, spray coating, dip coating, or doctor's blading.

In some embodiments, the squaraine compounds may be sublimed during vacuum deposition one or more times. As used herein, sublimation may include but is not limited to vacuum deposition. Accordingly, sublimation may be carried out at any temperature and pressure suitable for depositing the materials. Subliming the squaraine compounds may afford certain benefits regarding purification. Subliming squaraines one or more times may provide amorphous films and better properties than non-sublimed films. While not being bound by any theory, it is believed that multiple sublimation steps act as purification steps, for example, to remove trapping impurities otherwise present, whether the resulting film is amorphous or crystalline.

In one embodiment, the squaraine compound of formula (I) is deposited at a rate ranging from 0.1 to 1.5 Å/sec, such as 0.2 to 1.0 Å/sec, or even 0.2 to 0.6 Å/sec. In one embodiment, the deposited squaraine compound of formula (I) has a thickness of 100 Å or less, such as 65 Å or less, even 50 Å or less. As used herein the "thickness" refers to the thickness of the layer (e.g., the thickness of the layer of the squaraine compound) as opposed to the molecular characteristics (e.g., bond distances) of materials that form any given layer.

It should be appreciated that the squaraine materials described herein can be a good donor in any device architecture. Non-limiting mention is made to the squaraine material being used in an architectural arrangement chosen from planar, bulk heterojunctions, hybrid-planar mixed, nanocrystalline bulk heterojunctions, and the like. In some embodiments, this material may be a good donor toward $C_{50}$ in any device architecture. In other embodiments, the squaraines described herein may also be a good donor for other acceptors. In addition, if the energies are chosen correctly and it transports electrons, the disclosed squaraines could even be an acceptor for a given donor, again in a range of device architectures, such as those previously mentioned.

It is to be appreciated that the heterojunction according to the present disclosure may comprise at least two different squaraine compounds described herein, such as mixture of two different squaraines. Thus, there are also described methods of making such a device comprising a mixture of two, or more different squaraines.

In one embodiment, the deposited squaraine compound forms a discontinuous layer. As used herein, the term "discontinuous layer" is intended to mean a layer (e.g., a layer of a squaraine compound) that does not have a uniform thickness throughout the layer. In one embodiment, the discontinuous layer of the invention is a layer that does not completely cover all portions of the layer (or substrate) onto which it was deposited, thereby resulting in some portions of that layer being exposed after depositing the discontinuous layer.

In another embodiment, the deposited squaraine compound forms isolated nanoscale domains. As used herein "isolated nanoscale domains" is used to contrast uniform thin film, and thus refers to a portion of the deposited squaraine compound that exists as 1-50 nm domains, forming a discontinuous thin film.

In one embodiment, $C_{60}$ is deposited such that it is in contact with the squaraine compound in the organic photosensitive optoelectronic device. In another embodiment the squaraine layer is ultrathin, such that the $C_{60}$ has direct contact with the substrate.

The organic photosensitive optoelectronic devices described herein may function as a device or solar cell, photodetector or photoconductor. Whenever the organic photosensitive optoelectronic devices function as a PV device, the materials used in the photoconductive organic layers and the thicknesses thereof may be selected, for example, to optimize the external quantum efficiency of the device. Whenever the organic photosensitive optoelectronic devices function as photodetectors or photoconductors, the materials used in the photoconductive organic layers and the thicknesses thereof may be selected, for example, to maximize the sensitivity of the device to desired spectral regions.

This result may be achieved by considering several guidelines that may be used in the selection of layer thicknesses. It is desirable for the exciton diffusion length, $L_D$, to be greater than or comparable to the layer thickness, L, since it is believed that most exciton dissociation will occur at an interface. If $L_D$ is less than L, then many excitons may recombine before dissociation. It is further desirable for the total photoconductive layer thickness to be of the order of the electromagnetic radiation absorption length, $1/\alpha$, where $\alpha$ is the absorption coefficient, so that nearly all of the radiation incident on the PV device is absorbed to produce excitons. Furthermore, the photoconductive layer thickness should be as thin as possible to avoid excess series resistance due to the high bulk resistivity of organic semiconductors.

Accordingly, these competing guidelines inherently require tradeoffs to be made in selecting the thickness of the photoconductive organic layers of a photosensitive optoelectronic cell. Thus, on the one hand, a thickness that is comparable or larger than the absorption length is desirable (for a single cell device) in order to absorb the maximum amount of incident radiation. On the other hand, as the photoconductive layer thickness increases, two undesirable effects are increased. One is that due to the high series resistance of organic semiconductors, an increased organic layer thickness increases device resistance and reduces efficiency. Another undesirable effect is that increasing the photoconductive layer thickness increases the likelihood that excitons will be generated far from the effective field at a charge-separating interface, resulting in enhanced probability of geminate recombination and, again, reduced efficiency. Therefore, a device configuration is desirable which balances between these competing effects in a manner that produces a high external quantum efficiency for the overall device.

As noted, the organic photosensitive optoelectronic devices described herein may function as photodetectors. In this embodiment, the device may be a multilayer organic device, for example as described in U.S. Pat. No. 6,972,431, incorporated herein by reference in its entirety. In this case an external electric field may be generally applied to facilitate extraction of the separated charges.

A concentrator or trapping configuration may be employed to increase the efficiency of the organic photosensitive optoelectronic device, where photons are forced to make multiple passes through the thin absorbing regions. U.S. Pat. Nos. 6,333,458 and 6,440,769, incorporated herein by reference in their entirety, addresses this issue by using structural designs that enhance the photoconversion efficiency of photosensitive optoelectronic devices by optimizing the optical geometry for high absorption and for use with optical concentrators that increase collection efficiency. Such geometries for photosensitive devices substantially increase the optical path through the material by trapping the incident radiation within a reflective cavity or waveguiding structure, and thereby recycling light by multiple reflections through the photoresponsive material. The geometries disclosed in U.S. Pat. Nos. 6,333,458 and 6,440,769 therefore enhance the external quantum efficiency of the devices without causing substantial increase in bulk resistance.

Included in the geometry of such devices is a first reflective layer; a transparent insulating layer which should be longer than the optical coherence length of the incident light in all dimensions to prevent optical microcavity interference effects; a transparent first electrode layer adjacent the transparent insulating layer; a photosensitive heterostructure adjacent the transparent electrode; and a second electrode which is also reflective. In one embodiment, one or more coatings may be used to focus optical energy into desired regions of a device. See, e.g., U.S. Pat. No. 7,196,835, the disclosures of which, specifically related to such coatings, are herein incorporated by reference.

Various devices made according to the foregoing disclosures were made and tested. Results of these tests are provided in Tables 1 and 2, below.

TABLE 1

Extinction coefficients of aryl squaraines

| Squaraines | λmax(nm) | Extinction coefficient (cm$^{-1}$ M$^{-1}$) |
|---|---|---|
| SQ | 652 | 4.09 × 10$^5$ |
| DPSQ | 674 | 1.94 × 10$^5$ |
| 1-NPSQ | 666 | 2.04 × 10$^5$ |
| 2-NPSQ | 687 | 1.94 × 10$^5$ |

TABLE 2a

Photophysics data of SQ-ME in select solvents.

| Solvent | Stoke shift(nm) | Quantum yield (%) |
|---|---|---|
| MeCN | 15 | 73 |
| 2MeTHF | 11 | 77 |
| Toluene | 11 | 80 |
| Cyclohexane | 8 | 81 |

TABLE 2b

Photophysics data of aryl squaraines in select solvents.

| Solvent | Stoke Shift (nm) DPSQ | Quantum Yield DPSQ | Stoke Shift (nm) 1-NPSQ | Quantum Yield 1-NPSQ | Stoke Shift (nm) 2-NPSQ | Quantum Yield 2-NPSQ |
|---|---|---|---|---|---|---|
| 2MeTHF | 79 | 0.5 | 15 | 5.5 | 12 | 0.1 |
| Toluene | 79 | 28.7 | 61 | 36 | 80 | 6.5 |
| Cyclohexane | 56 | 55.1 | | | 64 | 10.1 |

TABLE 2c

Photophysics data of asymmetric aryl squaraines in select solvents.

| Solvent | Stoke Shift (nm) DPSQ | Quantum Yield DPSQ | Stoke Shift (nm) 1-NPSG | Quantum Yield 1-NPSG |
|---|---|---|---|---|
| 2MeTHF | 53 | 0.4 | 100 | 1.1 |
| Toluene | 80 | 6.5 | 58 | 0.9 |
| Cyclohexane | 64 | 10.1 | 35 | 0.3 |

The embodiments described herein are further illustrated by the following non-limiting examples:

Example 1

CBZSQ: 2,4-bis[4-N-carbazolo-2,6-dihydroxyphenyl] squaraine

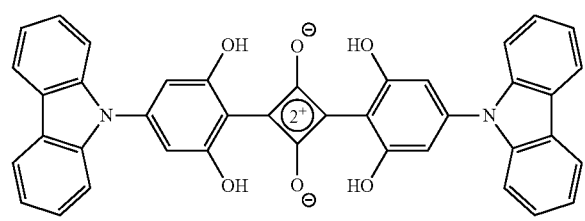

$^1$H-NMR (CDCl$_3$, 500 MHz): 8.51 (s, 2H), 7.99 (d, 2H), 7.53 (d, 1H), 7.32 (m, 2H), 7.21 (m, 2H), 7.01 (m, 2H), 6.67 (s, 2H)

Example 2

DPSQ: 2,4-bis[4-(N,N-diphenylamino)-2,6-dihydroxyphenyl] squaraine

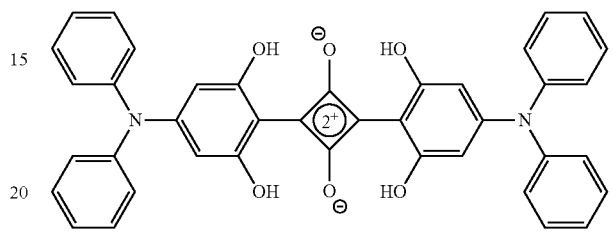

$^1$H-NMR (CDCl$_3$, 500 MHz): 10.1 (s, 1H), 7.41 (t, 2H, J=7.5 Hz), 7.29 (t, 1H, J=5 Hz), 7.23 (d, 2H, J=5 Hz), 5.87 (s, 1H)

$^{13}$C-NMR (CDCl3, 500 MHz): 31.29, 50.78, 98.75, 104.96, 127.57, 129.81, 144.08, 159.51, 163.06, 181.36

MS: m/z 632.2 (MH$^+$).

Example 3

1NPSQ: 2,4-bis[4-(N-Phenyl-1-naphthylamino)-2,6-dihydroxyphenyl] squaraine

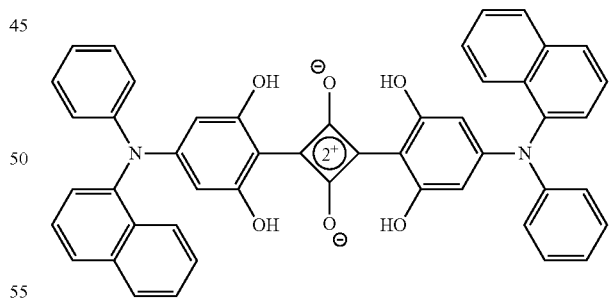

$^1$H-NMR (CDCl3, 400 MHz): 10.90 (s, 2H), 7.81-7.88 (, 3H), 7.44-7.48 (m, 3H), 7.26-7.29 (m, 4H), 5.71 (s, 2H). MS: m/z 732.2 (M$^+$-CH$_3$).

Example 4

2NPSQ: 2,4-bis[4-(N-Phenyl-2-naphthylamino)-2,6-dihydroxyphenyl] squaraine

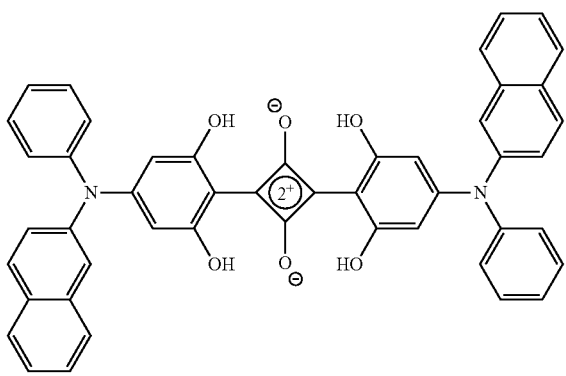

$^1$H-NMR (CDCl3, 400 MHz): 10.95 (s, 2H), 7.79-7.83 (m, 2H), 7.61-7.71 (m, 2H), 7.45-7.47 (m, 2H), 7.27-7.38 (m, 4H), 5.89 (s, 2H). Elemental analysis for $C_{48}H_{36}N_2O_6$: calcd: C, 78.68, H, 4.4, N, 3.82. found: C, 78.74, H, 4.33, N, 3.84.

Example 5

USSQ: {2-[4-(N,N-diisobutylamino)-2,6-dihydroxyphenyl]-4-diphenylamino} squaraine

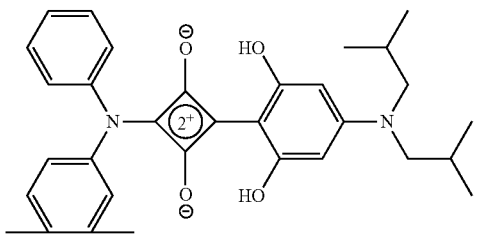

$^1$H-NMR (CDCl3, 400 MHz): 12.02 (s, 2H), 7.45-7.51 (m, 4H), 7.38-7.42 (m, 2H), 7.23-7.26 (m, 4H), 5.78 (s, 2H), 3.23 (d, 2H, J=8 Hz), 2.13 (m, 2H), 0.93 (d, 12H, J=6.8 Hz). Elemental analysis for $C_{30}H_{32}N_2O_4$: calcd: C, 74.36, H, 6.66, N, 5.78. found: C, 74.33, H, 6.75, N, 5.8.

Example 6

DPUSQ: {2-[4-(N,N-diphenylamino)-2,6-dihydroxyphenyl]-4-diphenylamino} squaraine

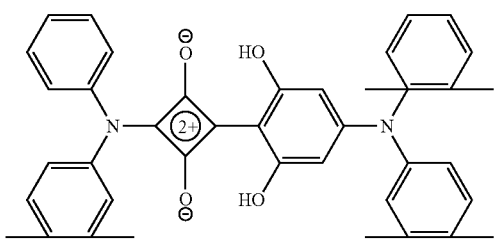

$^1$H-NMR (CDCl3, 500 MHz): 11.90 (s, 2H), 7.49 (m, 5H), 7.57 (m, 4H), 7.25 (m, 12H), 5.86 (s, 2H)

Example 7

Photovoltaic cells were grown on ITO-coated glass substrates that were solvent cleaned and treated in UV-ozone for 10 minutes immediately prior to loading into a high vacuum (~$3\times10^{-6}$ Torr) chamber. The organic materials CuPc (Aldrich), $C_{60}$ (MTR Limited), and 2,9-dimethyl-4,7-diphenyl-1,10-phenanthroline (BCP) (Aldrich) were purified by sublimation prior to use. Metal cathode materials such as Al (Alfa Aesar) were used as received. The squaraine solutions were prepared with different anhydrous solvents. The thickness of the squaraine layers was controlled via the concentration of squaraine solution. In this method, the donor layer was spin casted from squaraine solution on precleaned ITO substrates. The film was then transferred to the deposition chamber.

The other functional layers were sequentially grown by vacuum thermal evaporation at the following rates: $C_{60}$ (4 Å/sec), and 2,9-dimethyl-4,7-diphenyl-1,10-phenanthroline (BCP) (2 Å/sec) and metal: 1000 Å thick Al (2.5 Å/sec). The cathode was evaporated through a shadow mask with 1 mm diameter openings. Current-voltage (J-V) characteristics of PV cells were measured under simulated AM1.5G solar illumination (Oriel Instruments) using a Keithley 2420 3A Source Meter. The external quantum efficiency was also measured.

DPSQ formed shiny green crystals in the solid state. Compared with parent SQ, its solution absorption was red shifted to about 674 nm in dichloromethane (DCM) solvent. Comparatively, the spin casted DPSQ film covered a range of about from 550 nm to 800 nm. The solution processed DPSQ device was configured as ITO/DPSQ (x mg/ml)/C60 (400 Å)/ BCP (100 Å)/Al. With about 0.1 Ev deeper of a HOMO than the parent SQ, the DPSQ device generated about 200 mV higher Voc than SQ solution-processed devices. Three different solvents of chloroform, chlorobenzene and toluene were used to make different DPSQ solutions. The DPSQ film made with chloroform was the smoothest with RMS of about 1.1 nm, while the film with chlorobenzene and toluene exhibited an RMS of about 11 nm. The DPSQ device cast from chloroform generated the following results:

TABLE 3a

DPSQ/$C_{60}$ photovoltaic devices performance with different solvents

| DPSQ/$C_{60}$ Different solvents | $\eta_P$ (%) | $V_{oc}$ (V) | FF | $J_{sc}$ (mA/cm$^2$) |
|---|---|---|---|---|
| chloroform | 3.29 | 0.84 | 0.59 | 6.68 |
| Chlorebenzene | 0.41 | 0.55 | 0.27 | 2.33 |
| Toluene | 0.13 | 0.56 | 0.37 | 0.61 |

Figure 4:
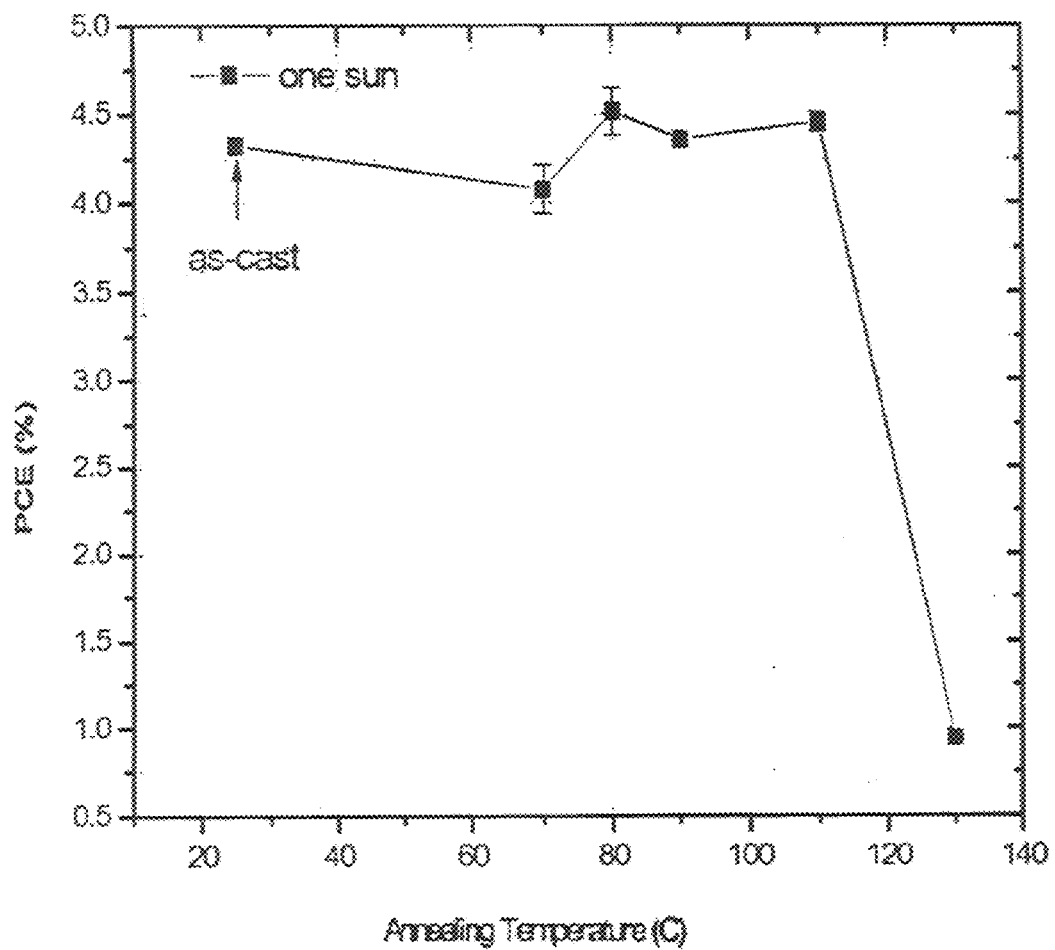
FIG. 4 illustrates the performance of a DPSQ device with different annealing temperatures, wherein the device has the structure ITO/MoO$_3$ (80 Å)/DPSQ (spin cast in N$_2$)/C$_{60}$ (400 Å)/BCP (100 Å)/Ag (1000 Å).

Table 3a. DPSQ/$C_{60}$ Photovoltaic Devices Performance with Different Solvents As shown in FIG. 4, different device performances resulted from thermally annealing the DPSQ as-cast films at different temperatures.

Figure 5:
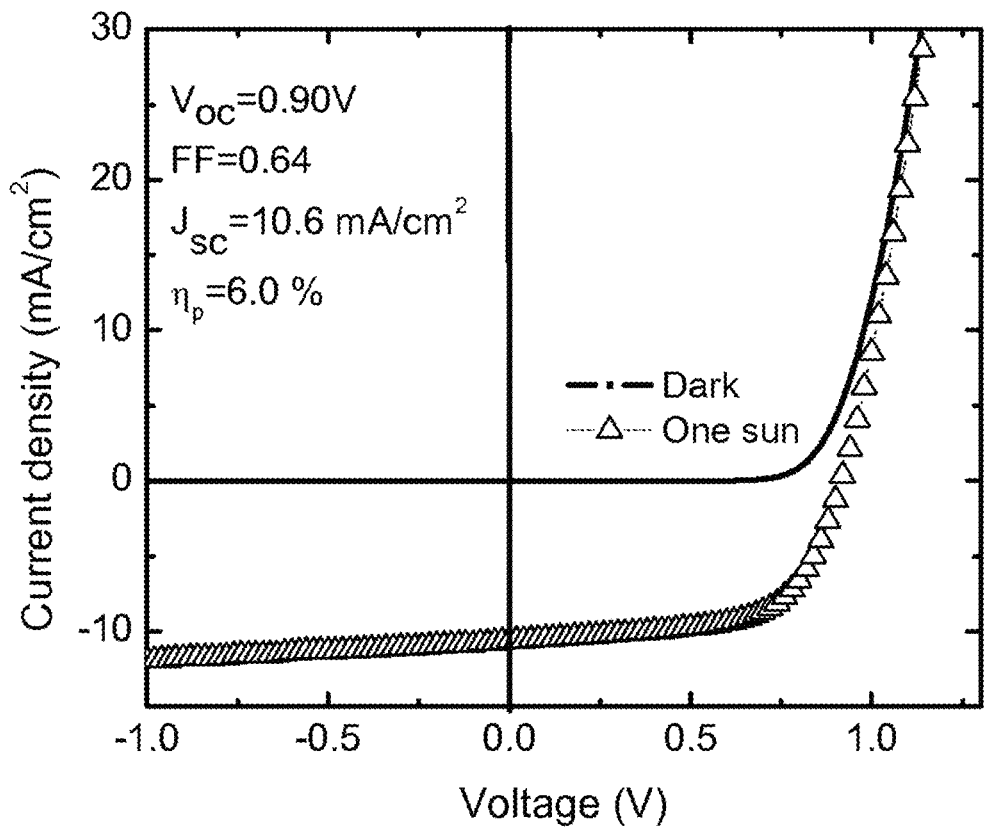
FIG. 5 illustrates the current density versus voltage (V) of a 1-NPSQ device annealed at 90° C., and having the structure ITO/MoO$_3$ (80 Å)/C$_{60}$ (10 Å)/1-NPSQ (200 Å)/C$_{60}$ (400 Å)/BCP (100 Å)/Ag (1000 Å).

Compared with DPSQ, 1-NPSQ and 2-NPSQ exhibit extended π conjugations, which may help to further enhance the charge transport ability of squaraine donors. The 1-NPSQ and 2-NPSQ are isomers with the same electrochemistry and similar optical property, but appear to behave quite different in devices. Compared with DPSQ, the UV- VIS absorption of 1-NPSQ is blue shifted to about 666 nm, while the 2-NPSQ is red shifted to about 686 nm in DCM solvent. The 1-NPSQ is more soluble, while the poorer solubility of 2-NPSQ may make film formation more challenging. A 1-NPSQ device was constructed as ITO/MoO$_3$ (80 Å)/1-NPSQ (x mg/ml)/C$_{60}$ (400 Å)/BCP (100 Å)/Al. The 1-NPSQ film was spin casted from the 1,2-dichlorobenzene solution and annealed at different temperatures for 10 minutes. With different temperature of 90° C., 110° C. and 130° C., the 90° C. appeared to be the best annealing temperature for 1-NPSQ, resulting in an efficiency of about 5.9%, with a Voc of about 0.85 V, Jsc of about 10.8 mA/cm$^2$, and FF of about 0.64. The efficiency reaches about 6% with a structure ITO/MoO$_3$ (80 Å)/C$_{60}$ (10 Å)/1-NPSQ (x mg/ml)/C$_{60}$ (400 Å)/BCP (100 Å)/Ag. As demonstrated in FIG. 5, one improvement appears to be the higher $V_{OC}$ of about 0.90 V. It is believed that the relative poor film quality of the 2-NPSQ film was responsible for the decreased efficiency of 2.9% observed with the 2-NPSQ device, with a $V_{OC}$ of about 0.87 V, Jsc of about 6.72 mA/cm$^2$, and FF of about 0.5.

With the symmetrical squaraines, donors absorb in the red region. Absorptions may be tuned to the blue and green regions of the spectrum by making the squaraine unsymmetrical. The unsymmetrical USSQ and DPUSQ exhibit absorption at 529 nm and 535 nm respectively. They have been demonstrated as effective donors in solution processed PVs. The USSQ and DPUSQ exhibit a deeper HOMO than DPSQ, and are believed to have relatively high $V_{OC}$ but low $J_{SC}$ due to sharp absorption in the range of 500-600 nm, and thus poor spectral overlap with the AM1.5 spectrum. This is the absorption range where a gap is observed in the spectral response of the of aryl SQ/C$_{60}$ devices.

Figure 6:
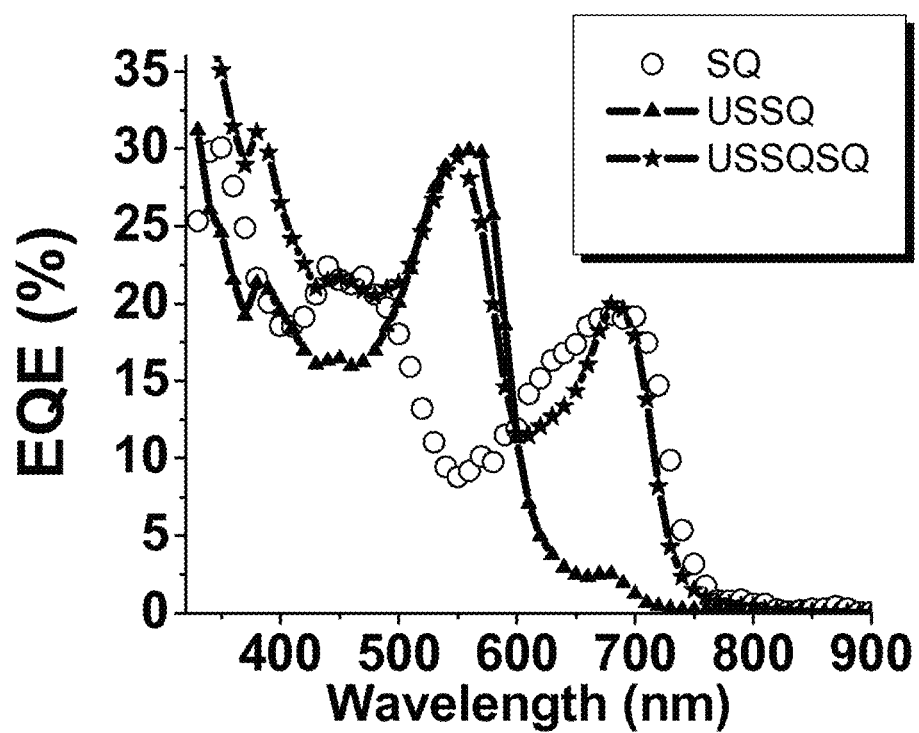
FIG. 6 illustrates the external quantum efficiency (EQE) of SQ, USSQ, and blended devices.

Exemplary blends of SQ and USSQ are shown in FIG. 6. Blends of DPUSQ or USSQ with symmetrical squaraines were also tested. The blending idea may be applied in both the vapor deposited and solution process techniques. With 1:1 weight ratio of DPUSQ and 1-NPSQ, device efficiencies were observed at about 2.38% without losing the FF of about 0.52. The Voc and $J_{SC}$ are about 0.81 V and about 5.43 mA/cm$^2$. The change of $V_{OC}$ is expected because of different morphology is generated by mixing two donors. However, the new USSQ and DPUSQ are conductive enough to be mixed with aryl squaraines. Thus, blending does not appear to lead to any loss in the $V_{oc}$ value. As expected, the high $J_{sc}$ is achieved. With both unsymmetrical and symmetrical squaraines, the visible solar spectra from 500-800 nm were covered. The usefulness of unsymmetrical squaraines could be potentially applied to other PVs which miss the coverage in the 500-600 nm.

It would be apparent to one of skill in the art that the present disclosure is not limited to solution processed devices, but can be extended to OPVs prepared by vapor deposition as well. While the above demonstrates, in part, a mixed donor approach in lamellar OPVs, it could be used in bulk heterojunction device structures as well, to increase the range of active wavelengths for the OPV. This device architecture, involving multiple donor materials in a single layer could be extended to the acceptor layer as well. Because of the good charge carrier mobility of squaraines, both the red and green region SQs could be mixed with other solar cell donors, such as SubPc or Porphyrins to extend the active wavelength range even further.

Figure 7:
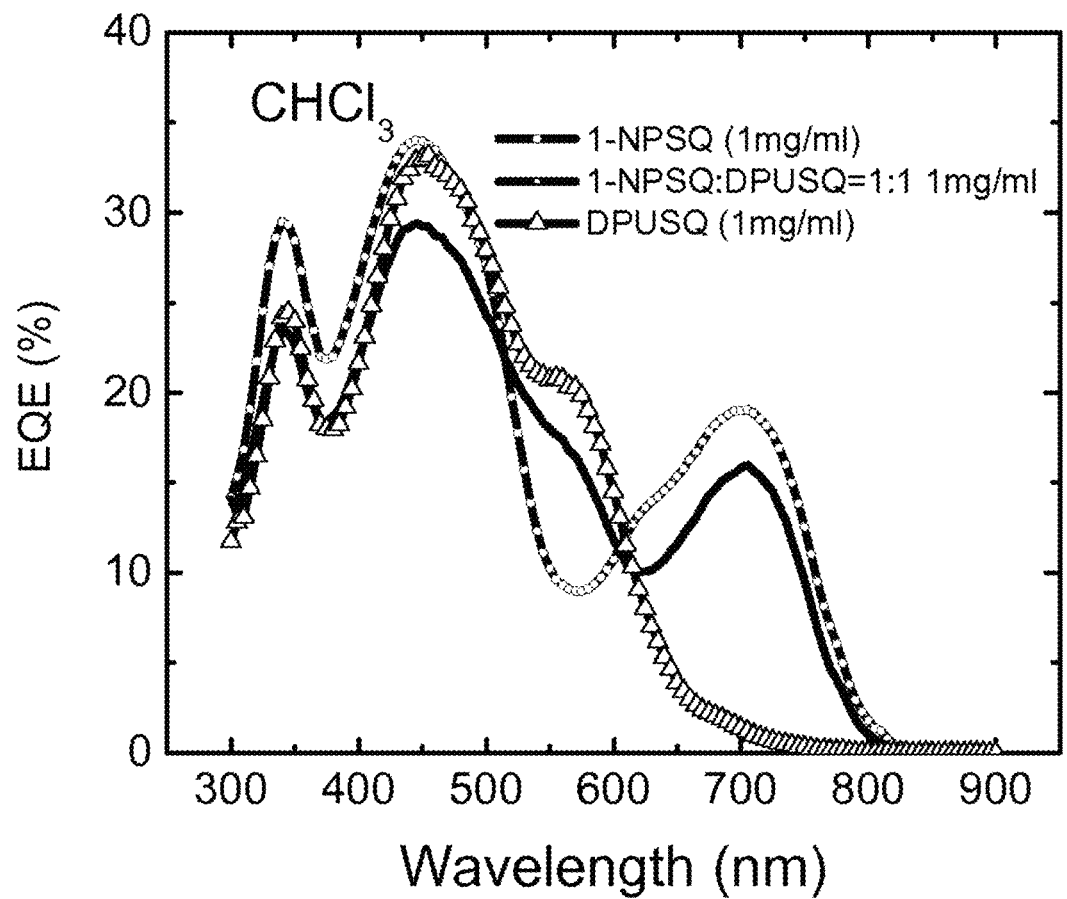
FIG. 7 illustrates the EQE of 1-NPSQ, DPUSQ, and blended devices.

As demonstrated in FIG. 7, high performances were achieved by blending the DPUSQ and 1-NPSQ with device structure ITO/MoO$_3$ (80 Å)/1-NPsQ: DPUSQ (1:11 mg/ml)/C$_{60}$ (400 Å)/PTCBI (80 Å)/Ag. From the EQE response plot, a contribution from both 1-NPSQ and DPUSQ was observed, along with the following characteristics;

TABLE 3b

Device performance for 1-NPSQ, DPUSQ and 1-NPSQ:DPUSQ cells.

| Doner (1 mg/ml) | $\eta_P$ (%) | $V_{oc}$ (V) | FF | $J_{sc}$ (mA/cm$^2$) |
|---|---|---|---|---|
| 1-NPSQ | 4.1 | 0.92 | 0.70 | 6.3 |
| DPUSQ | 4.0 | 0.99 | 0.74 | 3.4 |
| 1-NPSQ:DPUSQ | 5.2 | 0.98 | 0.71 | 7.46 |

Unless otherwise indicated, all numbers expressing quantities of ingredients, reaction conditions, and other properties or parameters used in the specification are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A squaraine compound of formula I:

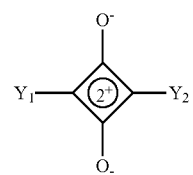

(I)

wherein,
Y$_1$ and Y$_2$ are independently chosen from —NR$_3$R$_4$ and a group of formula II

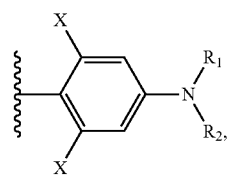

(II)

wherein X for each occurrence is independently chosen from hydrogen and hydroxyl;
R$_1$ and R$_2$ are taken together with any intervening atoms to form a group chosen from optionally substituted heteroaryl and optionally substituted heterocyclyl;
wherein one of Y$_1$ or Y$_2$ is —NR$_3$R$_4$;
R$_3$ and R$_4$ are taken together with any intervening atoms to form a group chosen from optionally substituted heteroaryl and optionally substituted heterocyclyl, and the optionally substituted heteroaryl and the optionally substituted heterocyclyl are independently chosen from monocyclic and multicyclic groups.

2. The compound of claim 1, wherein $Y_1$ is —$NR_3R_4$.

3. The compound of claim 1, wherein $Y_2$ is chosen from a group of formula II

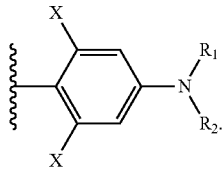

(II)

4. The compound of claim 3, wherein $Y_1$ is —$NR_3R_4$ and the optionally substituted heteroaryl and the optionally substituted heterocyclyl are independently chosen from monocyclic and multicyclic groups.

5. A squaraine compound of the formula:

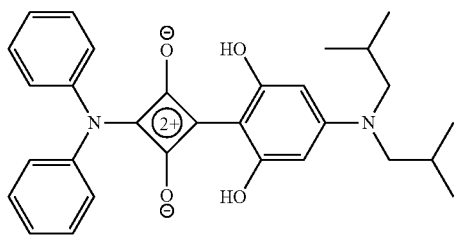

{2-[4-(N,N-diisobutylamino)-2,6-dihydroxyphenyl]-4-diphenylamino} squaraine (USSQ).

6. The compound of claim 3, wherein the group of formula II is chosen from a group of formula III:

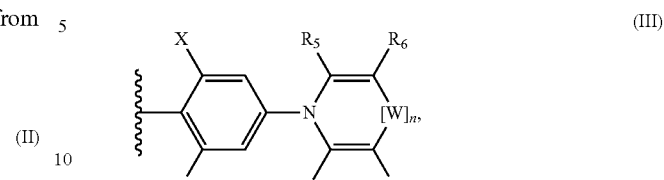

(III)

wherein
W is chosen from S, O, Se, and Te;
n is an integer chosen from 0 and 1; and
$R_5$ and $R_6$ are independently chosen from optionally substituted amino, cyano, halo, mercapto, optionally substituted alkenyl, optionally substituted alkynyl, optionally substituted alkyl, optionally substituted aryl, and optionally substituted heteroaryl, optionally substituted heterocyclyl, and optionally substituted carbocyclyl, or
$R_5$ and $R_6$ attached to adjacent atoms are taken together with any intervening atoms to form a group chosen from optionally substituted aryl, optionally substituted heteroaryl, optionally substituted carbocyclyl, and optionally substituted heterocyclyl.

7. The compound of claim 1, wherein $Y_2$ is —$NR_3R_4$.

8. An organic photosensitive optoelectronic device comprising at least one compound of claim 1, wherein the device comprises at least one donor-acceptor heterojunction.

9. A squaraine compound of the formula:

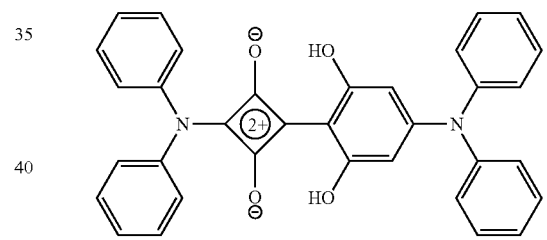

{2-[4-(N,N-diphenylamino)-2,6-dihydroxyphenyl]-4-diphenylamino} squaraine (DPUSQ).

* * * * *